United States Patent [19]

Kamenka et al.

[11] Patent Number: 5,248,686
[45] Date of Patent: Sep. 28, 1993

[54] SUBSTITUTED CYCLIC AMINES AND PHARMACEUTICAL COMPOSITION CONTAINING THEM

[75] Inventors: Jean-Marc Kamenka, Montpellier; Alain Privat, St Clement la Riviere; Robert Chicheportiche, Montpellier; Jean Costentin, Rouen, all of France

[73] Assignee: Centre National de la Recherche Sientifique, France

[21] Appl. No.: 883,885

[22] Filed: May 12, 1992

Related U.S. Application Data

[63] Continuation of Ser. No. 540,355, Jun. 19, 1990, abandoned.

[30] Foreign Application Priority Data

Jun. 29, 1989 [FR] France .................. 89 08704

[51] Int. Cl.$^5$ ................ A61K 31/445; C07D 405/04; C07D 409/04; C07D 491/113
[52] U.S. Cl. .................... 514/324; 514/252; 514/253; 514/278; 514/317; 514/320; 514/443; 514/462; 514/469; 544/360; 544/376; 544/410; 546/19; 546/187; 546/196; 546/202; 546/205; 549/49; 549/430; 549/462; 564/307; 564/308
[58] Field of Search ............. 546/19, 196, 202, 205, 546/187; 514/320, 324, 325, 278, 317, 252, 253, 647; 549/49, 430, 462; 544/360, 376, 410; 564/307, 308

[56] References Cited

FOREIGN PATENT DOCUMENTS

0317953 5/1989 European Pat. Off. .

OTHER PUBLICATIONS

Thurkauf et al "Syntheis and . . . " J. Med Chem. 33 1452–1458 (1990, May).
Iorio et al "Nitrogen Analog of Phencyclidine" CA 101: 143552w (1984).
Chemical Abstracts, vol. 110, No. 17, Apr. 24, 1989, p. 78, resume No. 147750t, Columbus, Ohio; J. M. Sani et al., Interactions of Phencyclidine and Two Derivatives with Serotonergic Receptors, & Sigma Phencyclidine--Like Comd. Mol. Probes Biol., (Proc. U.S.-Fr. Sponsored Int. Semin., 2nd 1987 (Pub. 1988) 209-14.
Chemical Abstracts, vol. 109, No. 3, Jul. 18, 1988, p. 44, resume No. 16882u, Columbus, Ohio; J. Vignon et al.: "[3H]N-[1-(2Benzo(b)Thiophenyl)Cyclohexy] Piperidine ([3H]BTCP): A New Phencyclidine Analog Selective For The Dopamine Uptake Complex", & Eur. J. Pharmacol. 1988, 148(3), 427-36.
Chemical Abstracts, vol. 110, No. 23, Jun. 5, 1989, p. 53, resume No. 205446m, Columbus, Ohio; M. Slimani et al.: "Neurochemical and Behavioral Evidence For A Central Indirect Dopaminergic Agonist Activity of GK 13, A Phencyclidine Derivative", & Sigma Phencyclidine-Like Cmpd. Mol. Probes Biol., [Proc. U.S.-FR. Sponsored Int. Semin.] 2nd 1987 (Pub. 1988), 511-20.

Primary Examiner—Alan L. Rotman
Assistant Examiner—Celia Chang
Attorney, Agent, or Firm—Pearne, Gordon, McCoy & Granger

[57] ABSTRACT

The invention relates to substituted arylamines and heteroarylamines, their preparation process and the pharmaceutical composition containing them. Said substituted amine is in accordance with the formula:

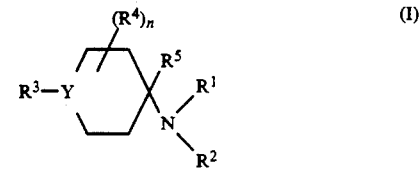

in which $R^1$ and $R^2$ are optionally substituted alkyl radicals or form with N an optionally substituted piperazine or piperidine cycle, $R^3$ and $R^4$ represent a hydrogen atom or an organic radical, Y represents $CR^6$ or N and $R^5$ is an optionally substituted benzothiophenyl, benzofuranyl or naphthyl radical.

These amines can be used in pharmaceutical compositions for the treatment of nervous depression or for stimulating vigilance.

13 Claims, No Drawings

SUBSTITUTED CYCLIC AMINES AND PHARMACEUTICAL COMPOSITION CONTAINING THEM

This is a continuation of application Ser. No. 07/540,355, filed Jun. 19, 1990, now abandoned.

The present invention relates to novel compounds having a structure similar to that of 1-(2-benzo(b)thiophenyl)1-piperidino)-cyclohexane (BTCP) of formula:

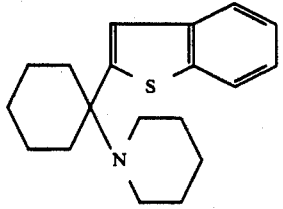

BTCP is a molecule derived from phencyclidine, which has properties differing from the latter as a result of the presence of the benzothiophenyl nucleus.

Phencyclidine(PCP), i.e. N-(1-phenylcyclohexyl)-piperidine of formula:

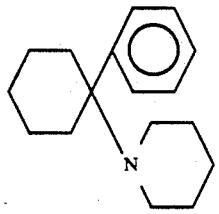

has been synthesized and studied for its pharmacological properties since 1958. As a result of these studies, it has been introduced as an analgesic and anesthetic under the name Sernyl and was then abandoned as a result of its psychodysleptic side effects.

Phencyclidine and most of its analogs or derivatives have in their behavioural pharmacological spectrum a dopaminergic component, incorrectly called an amphetaminic component by certain authors. Thus, it has been demonstrated that said component corresponds to an inhibition of the recapture of dopamine rather than a stimulation of release as in amphetamines. Thus, phencyclidine has an indirect dopaminergic action.

BTCP, which differs from PCP as a result of a benzothiophenyl nucleus in place of the phenyl nucleus has different properties, as has been described by J. Vignon et al in European Journal of Pharmacology, 148, 1988, pp. 427–436.

Thus, to a much greater extent BTCP has the capacity to inhibit the in vitro recapture of dopamine, whilst it has a very low affinity for the PCP receptor. This property makes BTCP of interest for other applications, e.g. in the field of antidepression and vigilance.

It has also been demonstrated by M. Slimani et al in Domino, E. F. and Kamenka, J. M. (eds.), Sigma and Phencyclidine-Like Compounds as Molecular Probes in Biology, NPP Books, Ann Arbor, 1988, pp. 511–520, that BTCP also had an inhibiting action of the same type on the recapture of noradrenaline.

Research has also been carried out to find molecules of the same type having the greatest possible dopaminergic action, but also and in particular a minimum affinity for the receptor of PCP.

The present invention specifically relates to novel substituted amines having these interesting properties.

According to the invention, the novel substituted amines comply with the formula:

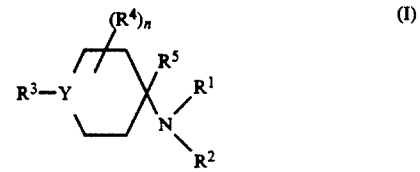

in which $R^1$ and $R^2$, which can be the same or different, represent an alkyl radical or an alkyl radical substituted by at least one substituent chosen from among the halogen atoms, the alkoxy radicals and the hydroxyl radical, or $R^1$ and $R^2$ form with the nitrogen atom to which they are bonded, a piperidine cycle optionally incorporating one or more substituents chosen from among OH, the aralkyl radicals, the alkyl radicals, the alkyl radicals substituted by at least one substituent chosen from among the halogen atoms and the hydroxy, alkoxy, arylalkoxy and oxycarbonylalkyl groups, the divalent radical

and $=O$, or in which $R^1$ and $R^2$ form together with the nitrogen atom to which they are bonded a piperazine cycle of formula:

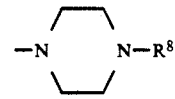

in which $R^8$ represents H, an aralkyl radical, an alkyl radical or an alkyl radical substituted by at least one substituent chosen from among the halogen atoms and the hydroxy, alkoxy, arylalkoxy and oxycarbonylalkyl groups, $R^3$ is a hydrogen atom or a radical chosen from among the alkyl, alkoxy and hydroxy radicals, $R^4$ is an alkyl, hydroxy or alkoxy radical, n is equal to 0 or is an integer from 1 to 8, whereby the $R^4$ can differ when $n \geq 2$, Y represents a nitrogen atom or $CR^6$ with $R^6$ representing a hydrogen atom, an alkyl radical, a hydroxy radical or an alkoxy radical, provided that $R^3$ represents a hydrogen atom or an alkyl radical when Y represents a nitrogen atom and $R^5$ represents a radical chosen from among the radicals complying with the formulas:

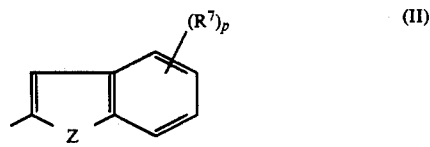

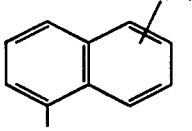

(III)

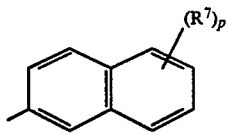

(IV)

in which Z is a sulphur or oxygen atom, R⁷ is an alkyl radical, p is equal to 0, 1 or 2 and the R⁷ can be different when p=2, provided that $R^3$ does not represent a hydrogen atom when Y represents —CH, $R^5$ represents

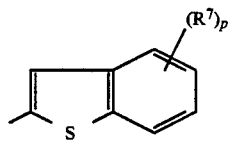

n and p are equal to 0 and $R^1$ and $R^2$ form together with the nitrogen atom to which they are bonded an unsubstituted piperidine cycle.

The aforementioned amines differ from BTCP either by the presence of substituents on the cyclohexyl, aromatic and/or piperidine nucleus, or by the replacement of the piperidine nucleus by alkyl radicals, or by the replacement of the benzothiophenyl nucleus by a benzofuranyl or naphthyl nucleus.

As a result of these modifications, there is a significant improvement to the inhibiting power of recapture of dopamine and/or noradrenaline, whilst still having a low affinity for the site of the PCP.

When the substituents used in the invention are alkyl radicals, they can be straight or branched alkyl radicals preferably with 1 to 4 carbon atoms. In the case of $R^3$, preference is given to radicals having 1 or 2 carbon atoms. For $R^1$ and $R^2$ good results are obtained with 2 to 3 carbon atoms.

When the substituents used in the invention are aralkyl radicals, the alkyl part of these radicals preferably has 1 to 3 carbon atoms. Examples of these radicals are benzyl and diphenyl methyl radicals.

In certain cases, the alkyl radicals used for $R^1$, $R^2$ or as substituents of a piperidine or piperazine cycle can be substituted by at least 1 substituent chosen from among the halogen atoms and the alkoxy, hydroxy, arylalkoxy and oxycarbonylalkyl groups. The oxycarbonylalkyl radicals can comply with the formula R—COO—, in which R is an alkyl.

The halogens which can be used are fluorine, chlorine, bromine and iodine.

The alkoxy radicals used can be straight or branched and have 1 to 3 carbon atoms. Examples of such radicals are methoxy, ethoxy and propyloxy radicals.

In the oxycarbonylalkyl radicals, the alkyl radical can also be straight or branched and preferably has 1 to 3 carbon atoms. Examples of such radicals are:$CH_3$—COO, $C_2H_5$COO, $C_3H_7$COO.

Examples of substituted alkyl radicals used as substituents of a piperazine or piperidine cycle are —$CH_2CH_2OH$, —$CH_2CH_2OCH_2CH_2CH_3$ and —$CH_2$-$H_2OCH(C_6H_5)_2$. In the case of a piperazine cycle with $R^8$ representing a substituted alkyl radical

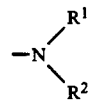

can comply e.g. with $R^2$ formulas given below:

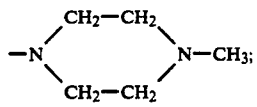

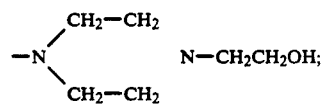

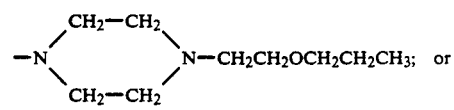

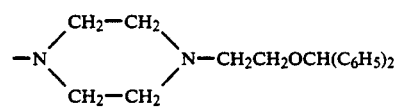

When $R^4$ represents OH and Y is a nitrogen atom, $R^4$ is preferably in the β position with respect to the nitrogen atom. In the same way, when

represents a piperidine cycle having an OH substituent, the latter is preferably not in the α position with respect to N.

When the substituents $R^3$, $R^4$ and $R^6$ are alkoxy radicals, it is possible to use those referred to hereinbefore.

According to a first embodiment of the invention, $R^5$ represents the radical of formula:

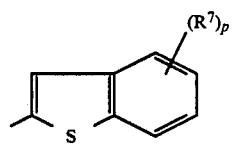

(V)

in which $R^7$ and p have the meanings given in claim 1.

Preferably, in this case, the benzothiophenyl nucleus is not substituted and p is equal to 0.

In this first embodiment, Y advantageously represents CH and consequently the substituted amines are derivatives of 1-benzothiophenyl-cyclohexyl amine.

In this case, good results are obtained when $R^1$ and $R^2$ represent a piperidine cycle and the latter is substituted in the 3 position and/or the cyclohexyl nucleus is substituted in the 4 position by an alkyl radical, preferably an ethyl or methyl radical.

Examples of such substituted amines are (benzo(b) thiophenyl-2)-1c-methyl-4-r-(piperidino-1)-1 cyclohexane, (benzo(b)thiophenyl-2)-1 (methyl-3 piperidino)-1)-1 cyclohexane, and (benzo(b)thiophenyl-2)-1 (dimethyl-3,5 piperidino)-1)-1 cyclohexane.

According to the invention, very good results are also obtained when $R^1$ and $R^2$ are alkyl radicals, e.g. propyl or ethyl radicals. In this case, it is not necessary for the benzothiophenyl or cyclohexyl nucleus to be substituted by alkyl groups.

Examples of such substituted amines are 1-(2-benzo(b)thiophenyl)-1-dipropylamino)-cyclohexane.

According to a second embodiment of the invention, $R^5$ is the radical of formula:

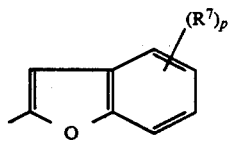

in which $R^7$ and p have the meanings given hereinbefore.

An example of such a substituted amine is 1-(2-benzo(b)furanyl)-1-(1-piperidino)-cyclohexane.

The substituted amines according to the invention can be prepared by different processes.

In the case of the substituted amines of formula (I)

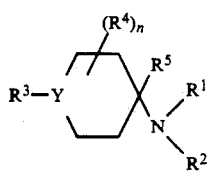

in which $R^1$ and $R^2$, which can be the same or different, represent an alkyl radical or an alkyl radical substituted by at least one substituent chosen from among the halogen atoms, the alkoxy radicals and the hydroxyl radical, or $R^1$ and $R^2$ form with the nitrogen atom to which they are bonded, a piperidine cycle optionally incorporating one or more substituents chosen from among OH, the aralkyl radicals, the alkyl radicals, the alkyl radicals substituted by at least one substituent chosen from among the halogen atoms and the hydroxy, alkoxy, arylalkoxy and oxycarbonylalkyl groups, the divalent radical

and=0, or in which $R^1$ and $R^2$ form together with the nitrogen atom to which they are bonded a piperazine cycle of formula:

in which $R^8$ represents H, an aralkyl radical, an alkyl radical or an alkyl radical substituted by at least one substituent chosen from among the halogen atoms and the hydroxy, alkoxy, arylalkoxy and oxycarbonylalkyl groups, $R^3$ is a hydrogen atom or a radical chosen from among the alkyl, alkoxy and hydroxy radicals, $R^4$ is an alkyl, hydroxy or alkoxy radical, n is equal to 0 or is an integer from 1 to 8, whereby the $R^4$ can differ when $n \geq 2$, Y represents a nitrogen atom or $CR^6$ with $R^6$ representing a hydrogen atom, an alkyl radical, a hydroxy radical or an alkoxy radical, provided that $R^3$ represents a hydrogen atom or an alkyl radical when Y represents a nitrogen atom and $R^5$ represents a radical chosen from among the radicals complying with the formulas:

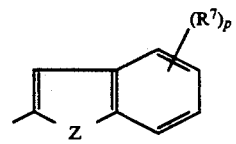

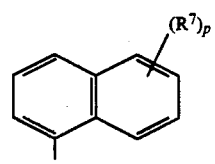

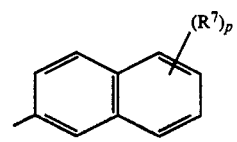

in which Z is a sulphur or oxygen atom, $R^7$ is an alkyl radical, p is equal to 0, 1 or 2 and the $R^7$ can be different when p=2, provided that $R^3$ does not represent a hydrogen atom when Y represents —CH, $R^5$ represents

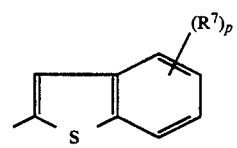

n and p are equal to 0 and $R^1$ and $R^2$ form together with the nitrogen atom to which they are bonded an unsubstituted piperidine cycle, it is possible to use a process consisting of:

a) preparing an α-aminonitrile of formula:

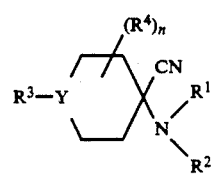

in which $R^1$, $R^2$, $R^3$, $R^4$, n and Y have the meanings given hereinbefore and b) reacting the thus prepared α-aminonitrile with a halide of formula: $MgXR^5$, in which X represents a halogen atom, excepting fluorine and $R^5$ has the meaning given hereinbefore.

When

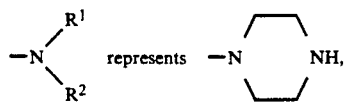

prior to the stage a), the NH group of the piperazine cycle is protected from the α-aminonitrile of formula (VII) by an appropriate radical, such as the acetile radical and the deprotection of said NH group takes place after stage b). According to this process, it is possible to prepare the α-aminonitrile of formula (VII) from cyclohexanones of formula (VIII):

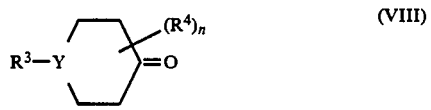

in which $R^3$, $R^4$, n and Y have the meanings given hereinbefore with an amine or piperidine of formula (IX):

in which $R^1$ and $R^2$ have the meanings given hereinbefore.

For this preparation, it is possible to react the acetone cyanohydrin (cyanide ion donor) with the amine or piperidine of formula (IX) and the cyclohexanone of formula (VIII) in the presence of magnesium sulphate, which acts as a dehydrating agent, in a solvent such as dimethyl acetamide (DMA). Following treatment and purification, the corresponding α-aminonitrile is isolated with a purity of at least 95% and it is possible to use it as it is for the second stage of the process, in which said α-aminonitrile of formula (VII) is reacted with the halide of formula $XR^5$ using the so-called Bruylants synthesis.

This synthesis consists of reacting the α-aminonitrile with a Grignard reagent obtained from the halide $XR^5$ in ether or anhydrous tetrahydrofuran (THF). Following an appropriate treatment and purification, the sought substituted amine is isolated. Anhydrous hydrochoric gas is then bubbled into an ethereal solution of the pure substituted amine and in this way the corresponding hydrosoluble hydrochloride is precipitated.

It is possible to prepare other addition salts to the acids by replacing the hydrochloric gas by the desired acid, e.g. sulphuric or tartaric acid. This synthesis route is stereospecific and consequently only gives access to one of the possible isomers.

The substituted amines obtained by this process, in which $R^1$ and $R^2$ form with the nitrogen atom to which they are bonded, a piperidine cycle having one or more constituents constituted by alkyl radicals substituted by a hydroxyl group, can be used for the preparation of substituted amines according to the invention in which $R^1$ and $R^2$ form with the nitrogen atom to which they are bonded, a piperidine cycle having one or more substituents constituted by alkyl radicals substituted by a halogen atom or by an oxycarbonylalkyl radical.

In this case, the hydroxyalkylated substituted amines are reacted with a halogenating agent or an appropriate carboxylic acid for replacing the hydroxyl group by a halogen atom or an oxycarbonylalkyl radical.

When the halogen atom is bromine, it is possible to use thionyl bromide as the halogenating agent. When the halogen atom is chlorine, thionyl chloride can be used. When the halogen atom is iodine, trimethyl silane iodide can be used.

When the substituent to be introduced is an oxycarbonylalkyl radical of formula OCOR with R representing an alkyl radical, the corresponding carboxylic acid RCOOH, a halide or an anhydride of said acid is used.

It is also possible to prepare the substituted amines of formula (I) of the invention in which $R^1$ and $R^2$ form with the nitrogen atom to which they are bonded, a piperidine cycle which is either unsubstituted or is substituted by at least one substituent chosen from among the alkyl radicals and alkyl radicals substituted by a halogen atom or the hydroxyl radical using a 4 stage process having the particular advantage of not being stereospecific and of permitting access to the two possible isomers.

This process consists:
a) of preparing an alcohol of formula:

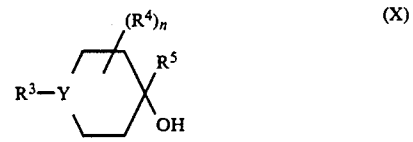

in which $R^3$, $R^4$, $R^5$, n and Y have the meanings indicated hereinbefore, b) of transforming the alcohol prepared in stage a) into a corresponding azide derivative of formula:

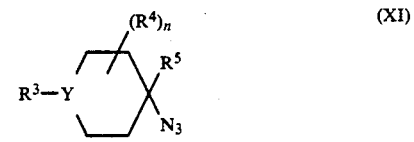

c) of reducing the azide derivative into a mixture of primary amines and
d) of reacting the mixture of primary amines with a 1,5-dihalogenopentane optionally having one or more substituents chosen from among alkyl radicals, alkyl radicals substituted by a halogen atom or a hydroxyl group.

Thus, this synthesis takes place in 4 stages, which are:
a) the preparation of the alcohol of formula (X), which can be carried out by reacting the cyclohexanone of formula (VIII)

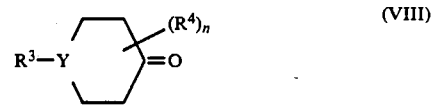

with a Grignard reagent obtained from the halides of formula $XR^5$ in anhydrous ether, which gives the corresponding alcohols which are subjected to a rapid purification and
b) the preparation of the corresponding azide derivatives of formula (XI).

This can be carried out by using a process similar to that used in the Schmidt and Curtius reactions, by carrying out the substitution of the alcohol function by the azide function by adding crude alcohols to a sodium azide suspension in trichloroacetic acid, or trifluoroacetic acid and chloroform in cold form. Following the treatment, isolation takes place of a crude mixture of epimeric azides and which is subsequently used as such. This is followed by c) reduction of the azides and for this purpose the preceding mixture can be reacted with Raney nickel in isopropanol in order to supply, after treatment, a mixture of epimeric primary amines used as such subsequently.

d) The final stage is the formation of the piperidine cycle and purification. For this stage hot reaction takes place in acetonitrile or ethanol of 1,5-dibromopentane optionally substituted by one or more substituents chosen from among the alkyl radicals and alkyl radicals substituted by a halogen atom or the hydroxyl group on the preceding mixture of primary amines. Following treatment, isolation takes place of a residue essentially containing a crude mixture of two epimers. It is possible to obtain the two pure isomers by chromatography. By bubbling anhydrous hydrochloric gas into the ethereal solutions of the thus separated amines, the corresponding hydrosoluble hydrochlorides are precipitated.

In an identical manner, it is possible to prepare addition salts to the acids other than the hydrochloride referred to hereinbefore.

As a result their indirect dopaminergic action, the substituted amines according to the invention can be used in pharmaceutical compositions, e.g. for the treatment of depression and for stimulating vigilance.

Thus, as will be shown hereinafter, the substituted amines according to the invention have a non-amphetaminic stimulating effect on the dopaminergic system by also stimulating the noradrenergic system, which makes it possible to treat nervous depression under good conditions.

The invention also relates to pharmaceutical compositions incorporating at least one substituted amine of formula (I) according to the invention, or its addition salt to a pharmaceutically acceptable acid. The acids which can be used are e.g. hydrochloric, sulphuric and tartaric acid.

For the preparation of pharmaceutical compositions, it is possible to dissolve an addition salt to the acids of the substituted amines according to the invention in an aqueous solution which is injectable or administrable by the oral route, e.g. physiological serum.

It is also possible to include these amines in solid preparations, such as tablets or orally administrable gelatin capsules by using standard excipients and methods.

These pharmaceutical compositions can incorporate excipients, diluents, plasticizers and other pharmaceutically acceptable additives such as those generally used in pharmaceutical preparations. The doses used can vary from 2.5 to 20 mg/kg of body weight, as a function of the administration route and the state of the patient.

For intramuscular or subcutaneous administration doses of 2.5 to 10 mg/kg can be used. For oral administration doses of 10 to 20 mg/kg can be used.

When the pharmaceutical composition is in the form of a solution, the amino derivative concentration of the solution is preferably such that the administered volume varies from 0.5 to 2 ml.

For these pharmaceutical compositions, it is possible to use the amines according to the invention in the form of their different isomers or a mixture of isomers. However, and as will be shown hereinafter, when the substituted amines according to the invention incorporate an alkyl substituent $R^3$ on a cyclohexyl nucleus, it is preferable to use the cis-isomer for the position of $R^3$ relative to the nitrogen atom of the piperidine cycle.

In the case where the substituted amine comprises an alkyl substituent $R^4$ in the 2 position of a cyclohexyl nucleus, it is preferable to use the cis-isomer for the position of $R^4$ relative to the nitrogen atom.

However, in the case where the substituted amine comprises an alkyl substituent $R^4$ in the 3 position of the cyclohexyl nucleus, it is preferable to use the trans-isomer.

Other features and advantages of the invention can be gathered from the following examples, which are obviously given in an illustrative and non-limitative manner.

Examples 1 to 11 illustrate the preparation of α-aminonitriles usable for preparing substituted amines according to the invention of examples 12 to 28 for a two-stage process. Examples 29 to 32 illustrate the preparation of the two substituted amine isomer forms using the 4 stage process. Examples 34 to 36 and 38 illustrate the properties of substituted amines according to the invention in in vitro tests, whilst examples 37 and 39 illustrate the activity of substituted amines according to the invention in an in vivo test.

EXAMPLE 1

Preparation of 1-cyano-1-(1-piperidino)-cyclohexane (synthon I)

15 g (0.15 mole) of cyclohexanone, 13.4 (0.15 mole) of acetone cyanohydrin, 55 g (0.45 mole) MgSO$_4$ (dried) are mixed into 26 g (0.3 mole) of piperidine and 8.7 g (0.1 mole) of dimethyl acetamide (DMA). The mixture obtained is stirred strongly at 45° C. and for 48 h, followed by pouring into a large volume of water and ice violently stirred for 30 min. Following ether extraction, drying on Na$_2$CO$_3$ and vacuum evaporation of the solvent a solid residue is obtained which, after crystallization in hexane or petroleum ether, gives 20.2 g (70%) of the synthon I in the form of an analytically prure white solid melting at 68° to 69° C. (IR 2200cm$^{-1}$, GC/MS: 100°-250° C. (20° C./min) RT=5.06 min, m/e 206.15)

The characteristics are as follows:

IR spectrometry: 2200 m$^{-1}$, mass spectrometry coupled with gas chromatography (GCIMS):
injector temperature: 100°-250° C. (20° C./min); retention time RT=5.06 min, m/e 206.15.

EXAMPLE 2

Preparation of 1-cyano-1-(3-methyl-1-piperidino)cyclohexane (synthon II)

3 g (0.039 mole) of cyclohexanone, 3.3 g (0.039 mole) of acetone cyanohydrin, 23.4 g (0.19 mole) of dried MgSO$_4$ are mixed into 5.77 g (0.058 mole) of 3-methylpiperidine and 5 g (0.058 mole) of DMA. The mixture is stirred strongly at 45° C. for 48 h and is then poured into a large volume of water and ice which is violently stirred for 30 min. Following ether extraction, drying on Na$_2$CO$_3$ and vacuum evaporation of the solvent, 7 g (87.5%) of synthon II are obtained in the form of a yellow oil with a purity greater than 95% and adequate for the remainder of the syntheses (IR 2200cm$^{-1}$, GC/MS: 100°–250° C. (20° C./min), RT=4.75 min, m/e: 192.15.

EXAMPLE 3

Preparation of 1-cyano-1-(4-ethyleneketalpiperidino)-1-cyclohexane (synthon III)

3.2 g (0.034 mole) of cyclohexane, 2.85 g (0.034 mole) of acetone cyanohydrin and 20.2 g (0.17 mole) of dried MgSO$_4$ are mixed into 7.16 g (0.05 mole) of 1,4-dioxa-8-azaspiro decane (4.5) and 4.4 g (0.05 mole) of DMA. The mixture is stirred strongly at 45° C. for 48 h and is then poured into a large volume of water and ice, which is violently stirred for 30 min. Following ether extraction, drying on Na$_2$CO$_3$ and vacuum evaporation of the solvent, 6 g of synthon III are obtained in the form of a solid white residue (73.5%) which melts at 108° to 109° C. (IR 2200 cm$^{-1}$, GC/MS: 100°–250° C. (20° C./min), RT=8.32min, m/e 250.15.

EXAMPLE 4

Preparation of 1-cyano-1-(3-hydroxymethylpiperidino)-1-cyclohexane (synthon IV)

8.83 g (0.09 mole) of cyclohexanone, 7.66 g (0.09 mole) of acetone cyanohydrin, 32.4 g (0.27 mole) of dried MgSO$_4$ are mixed with 20.7 g (0.18 mole) of 3-hydroxymethyl-piperidine and 10 ml of DMA. The mixture is stirred strongly at 45° C. for 48 h and isthen poured into a large volume of water and ice, which is violently stirred for 30 min. Extraction takes place with 3×250 ml of ether, drying takes place on Na$_2$SO$_4$ and vacuum evaporation is carried out to obtain 19 g of a yellowish solid residue. Successive crystallizations in ethanol precipitate 15 g (38% of synthon IV in the form of colourless crystals melting at 94° to 95° C. (IR 2200 cm$^{-1}$, GC/MS: 100°–250° C. (20° C./min), RT=8.14 min, m/e 222.15).

EXAMPLE 5

Preparation of 1-cyano-1-(3,5-dimethyl-piperidino)-1-cyclohexane (synthon V)

6 g (0.06 mole) of cyclohexanone, 5.2 g (0.06 mole) of acetone cyanohydrin and 22 g (0.18 mole) of dried MgSO$_4$ are mixed into 27.6 g (0.122 mole) of 3,5-dimethyl-piperidine and 11.3 g (0.13 mole) of DMA. The mixture is stirred strongly at 45° C. for 48 h and is then poured into a large volume of water and ice, which is violently stirred for 30 min. Following ether extraction, drying on Na$_2$CO$_3$, as well as vacuum evaporation of the solvent, 10 g (76%) of synthon V is obtained in the form of a whitish solid residue with a purity better than 95%, which is adequate for the remainder of the syntheses (IR 2200 cm$^{-1}$, GC/MS 100°–250° C. (20° C./min), RT=5.44 min, m/e 220.25).

EXAMPLE 6

Preparation of 4-cyano-1,2,2,6,6-pentamethyl-4-(1-piperidino)-piperidine (synthon V)

17.6 g (0.11 mole) of 1,2,2,6,6-pentamethyl-4-piperidinone, 9.5 g (0.11 mole) of acetone cyanohydrin and 50 g (0.42 mole) of dried MgSO$_4$ are mixed into 19.1 g (0.22 mole) of piperidine and 1 g of DMA. The mixture is stirred strongly at 45° C. for 48 h and is then poured into a large volume of water and ice, which is violently stirred for 30 min. The precipitate obtained is suction filtered, dried and crystallized in petroleum ether to give 31 g (92%) of synthon VI in the form of white crystals melting at 98° to 99° C. (analytically pure) (IR 2200 cm$^{-1}$).

EXAMPLE 7

Preparation of 1-cyano-1-(1-dipropylamino)-cyclohexane (synthon VII)

6.6 g (0.067 mole) of cyclohexane, 5.7 g (0.067 mole) of acetone cyanohydrin and 40.4 g (0.34 mole) of dried MgSO$_4$ are mixed into 10.2 g (0.1 mole) of dipropylamine and 5 ml of DMA. Strong stirring takes place at 45° C. for 48 h and then the mixture is poured into a large volume of water and ice, which is violently stirred for 30 min. Following extraction with ether, drying on Na$_2$CO$_3$ and evaporation of the solvent in vacuo, 10 g (71.3%) of synthon VII are obtained in the form of a yellowish oil with a purity higher than 95% and adequate for the sequence of the syntheses (IR 2200 cm$^{-1}$, GC/MS 100°–250° C. (20° C./min), RT=4.60 min, m/e 208.15).

EXAMPLE 8

Preparation of 1-cyano-1-(1-diethylamino)-cyclohexane (synthon VIII)

10.9 g (0.11 mole) of cyclohexanone, 9.44 g (0.11 mole) of acetone cyanohydrin and 40.4 g (0.34 mole) of dried MgSO$_4$ are mixed into 16.2 g (0.22 mole) of diethyl amine and 9.6 of DMA. Strong stirring takes place at 45° C. for 48 h and then the mixture is poured into a large volume of water and ice, which is violently stirred for 30 min. Following ether extraction, drying on Na$_2$CO$_3$ and vacuum evaporation of the solvent, 15 g (77.8%) of synthon VIII are obtained in the form of a yellowish oil with a purity better than 95% and adequate for the sequence of the syntheses (IR 2200cm$^{-1}$, GC/MS 100°–250° C. (20° C./min), RT=4.06 min, m/e 180.20).

EXAMPLE 9

Preparation of 1-cyano-1-(4-methyl-1-piperidino)-1-cyclohexane (synthon IX)

7.5 g (0.078 mole) of cyclohexanone, 6.6 g (0.078 mole) of acetone cyanohydrin and 46.8 g (0.38 mole) of dried MgSO$_4$ are mixed into 11.5 g (0.12 mole) of 4-methyl-piperidine and 10 g of DMA. Strong stirring takes place at 45° C. for 48 h and the mixture is then poured into a large volume of water and ice, which is violently stirred for 30 min. Following ether extraction, drying on Na$_2$CO$_3$ and vacuum evaporation of the solvent, 13 g (81.2%) of synthon IX are obtained in the form of a yellowish oil with a purity above 95% and adequate for the sequence of the syntheses (IR 2200cm$^{-1}$, GC/MS).

EXAMPLE 10

Preparation of 1-cyano-1-(3,5-dimethyl-1-piperidino)-4-methyl cyclohexane (synthon X)

4.8 g (0.04 mole) of 4-methyl-cyclohexanone, 3.6 g (0.04 mole) of acetone cyanohydrin and 15.4 g (0.13 mole) of dried MgSO$_4$ are mixed into 4.8 g (0.04 mole) of 3,5-dimethyl-piperidine and 3.6 g of DMA. Strong stirring takes place at 45° C. for 48 h and the mixture is then poured into a large volume of water and ice, which is violently stirred for 30 min. Following ether extraction drying on Na$_2$CO$_3$ and vacuum evaporation of the solvent, 7 g (70%) of synthon X are obtained in the form of a yellowish oil with a purity of better than 95% and sufficient for the remainder of the syntheses. It contains two epimeric aminonitriles which, in the following Bruylants reaction, epimerize to the thermodynamically stable compound which is the only one to react (IR 2200cm$^{-1}$, GC/MS: 100°–250° C. (20° C./min) RT=5.58 min, RT=5.62 min, m/e 234.10.

EXAMPLE 11

Preparation of
1-cyano-1-(3,5-dimethyl-1-piperidino)-3-methyl-cyclohexane (synthon XI)

4.8 g (0.04 mole) of 3-methyl-cyclohexanone, 3.6 g (0.04 mole) of acetone cyanohydrin and 15.4 g (0.13 mole) of dried MgSO$_4$ are mixed into 4.8 g (0.04 mole) of 3,5-dimethyl-piperidine and 3.6 g of DMA. Strong stirring takes place at 45° C. for 48 h and the mixture is then poured into a large volume of water and ice, which is violently stirred for 30 min. Following ether extraction, drying on Na$_2$CO$_3$ and vacuum evaporation of the solvent, 6 g (60%) of synthon XI is obtained in the form of a yellow oil with a purity higher than 95% and adequate for the remainder of the syntheses. It contains 2 epimeric aminonitriles which, in the following Bruylants reaction, epimerize towards the thermodynamically stable compound which is the only one to react (IR 2000 cm$^{-1}$, GC/MS: 100°–250° C. (20° C./min) RT=5.54 min, RT=5.68 min, m/e 234,10.

EXAMPLE 12

Preparation of
4-(2-benzo(b)thiophenyl)-1,2,2,6,6-pentamethyl-4-(1-piperidino)-piperidine (compound 1)

To a Grignard reagent prepared from 1.9 g (0.0076 mole) of 2-iodobenzo(b)thiophene and 0.36 g of magnesium in the form of turnings in 20 ml of anhydrous ether is added dropwise at ambient temperature 1 g (0.0038 mole) in 10 ml of anhydrous ether of synthon VI of example 6. The solution is refluxed for 16 h, then cooled and poured into a saturated solution of NH$_4$Cl and ice. After stirring for 30 min and decanting, the mixture is extracted with ether (3×15 ml) and then the ethers are washed with 15% HCl (3×15 ml). The combined aqueous phases are neutralized by 20% NH$_4$OH and extracted with ether (3×15 ml). The combined ethers are dried on Na$_2$SO$_4$ and evaporated under reduced pressure to give a whitish, yellow residue. Chromatography on Merck alumina (activity 2-3) in petroleum ether supplies 0.9 g of compound 1 in the form of a white solid (64.3%). By bubbling gaseous HCl into the ethereal solution of this compound, its white solid dihydrochloride is precipitated and which, recovered by suction filtering and vacuum drying, melts at 168°–169° C. (analytically pure).

The NMR spectrum of the $^{13}$C of this compound and its percentage analysis are given in the attached tables 2 and 3.

EXAMPLE 13

Preparation of
1-(2-benzo(b)thiophenyl)-3-methyl-1-piperidino)-1-cyclohexane (compound 2)

In 50 ml of anhydrous ether is prepared the Grignard reagent resulting from the action of 9.4 g (0.036 mole) of 2-iodobenzo(b)thiophene on 1.44 g (0.06 mole) of magnesium turnings. To it is slowly added 5 g (0.024 mole) of synthon II of example 2 dissolved in 50 ml of anhydrous ether. Stirring takes place for 12 h at reflux and the complex is decomposed by a cold saturated NH$_4$Cl solution and then, after decanting, the waters are extracted with ether (3×50 ml). The combined ethereal phases are extracted by a 20% aqueous HCl solution (2×50 ml). The acid waters are neutralized by NH$_4$OH, extracted with ether (3×50 ml) and the collected ethers, after drying on Na$_2$SO$_4$ are vacuum evaporated to give 6 g of a yellowish brown, solid residue. The latter undergoes chromatography on Merck alumina (activity 2-3) in a mixture of petroleum ether and ether (90/10 v/v to give 4.9 g (65%) of compound 2 in the form of a white solid melting at 85° to 86° C. By bubbling gaseous HCl into the ethereal solution of this compound, its white solid hydrochloride is precipitated and which, when recovered by suction filtering and vacuum drying, melts at 180° to 181° C. (analytically pure) (GC/MS of base; 100°–250° C., 15° C./min RT=17.70 min, m/e 313.2). The NMR spectrum of the $^{13}$C of this compound and its percentage analysis are given in the attached tables 2 and 3.

EXAMPLE 14

Preparation of
1-(2-benzo(b)thiophenyl)-1-(1-dipropylamino)-cyclohexane (compound 3)

In 50 ml 1 of anhydrous ether is prepared the Grignard reagent resulting from the action of 13 g (0.05 mole) of 2-iodobenzo(b)thiophene on 2 g (0.08 mole) of magnesium turnings. To it is slowly added 7 g (0.034 mole) of synthon VII of example 7 dissolved in 50 ml of anhydrous ether. Stirring takes place for 16 h at reflux, the complex is decomposed by a cold saturated NH$_4$Cl solution and then, after decanting, extraction takes place with ether (3×150 ml). The combined ethereal phases are extracted by an aqueous 20% HCl solution (2×200 ml). The acid waters are neutralized by NH$_4$OH, extracted with ether (3×150 ml) and the collected ethers, after drying on Na$_2$SO$_4$, undergo vacuum evaporation to give 8 g of a yellowish oily residue. The latter undergoes chromatography on Merck alumina (activity 2-3) in petroleum ether to give 7.4 g (69%) of compound 3 in the form of a colourless oil. By bubbling gaseous HCl into the ethereal solution of this compound, its white solid hydrochloride is precipitated and which, when recovered by suction filtering and vacuum drying, melts at 157°–158° C. (analytically pure). (GC/MS of base: 100°–250° C. (20° C./min) RT=9.58 min, m/e 315.15.

The NMR spectrum of the $^{13}$C of this compound and its percentage analysis are given in the attached tables 2 and 3.

EXAMPLE 15

Preparation of
1-(2-benzo(b)furanyl)-1-(1-piperidino)-cyclohexane (compound 4)

The Grignard reagent resulting from the action of 7.3 g (0.03 mole) of 2-iodobenzo(b)furan on 1.2 g (0.05 mole) of magnesium turnings is prepared in 70 ml of anhydrous ether. To it are slowly added 4 g (0.02 mole) of synthon I of example 1 dissolved in 70 ml of anhydrous ether. Stirring takes place for 16 h at reflux, the complex is decomposed by a cold saturated $NH_4Cl$ solution and then, after decanting, extraction takes place with ether (3×100 ml). The combined ethereal phases are extracted by an aqueous 20% HCl solution (3×100 ml). The acid waters are neutralized by $NH_4OH$, extracted with methylene chloride (2×70 ml) and then with ether (2×70 ml). The collected ethers, after drying on $Na_2SO_4$, undergo vacuum evaporation to give 2.5 g of a yellowish solid residue. The latter undergoes chromatography on Merck alumina (activity 2-3) in petroleum ether containing ether (90/10 v/v) to give 2 g (35%) of compound 4 in the form of a white solid melting at 74°-75° C. By bubbling gaseous HCl into the ethereal solution of this compound, its solid white hydrochloride is precipitated and when recovered by suction filtering and vacuum drying melts at 194°-195° C. (analytically pure). (GC/MS of base: 70°-250° C. (15° C./min) RT=14.82 min, m/e 283.20.

The NMR spectrum of the $^{13}C$ of this compound and its percentage analysis are given in the attached tables 2 and 3.

EXAMPLE 16

Preparation of
1-(2-benzo(b)thiophenyl)-4-(ethyleneketal-1-piperidino)-cyclohexane (compound 5)

The Grignard reagent resulting from the action of 7.3 g (0.03 mole) of 2-iodobenzo(b)thiophene on 1.2 g (0.05 mole) of magnesium turnings is prepared in 50 ml of anhydrous ether. To it are slowly added 5 g (0.02 mole) of synthon III of example 3 dissolved in 30 ml of anhydrous ether. Stirring takes place for 16 h at reflux, the complex is decomposed by a cold saturated $NH_4Cl$ solution and then, after decanting, the waters are extracted with ether (3×60 ml). The combined ethereal phases are washed with distilled water (2×100 ml) and, after drying on $Na_2SO_4$ undergo vacuum evaporation to give 5 g of a whitish solid residue. The latter undergoes chromatography on Merck alumina (activity 2-3) in petroleum ether to give 4 g of compound 5 in the form of a white solid (56%) melting at 80°-81° C. By bubbling gaseous HCl into the ethereal solution of said compound, its solid white hydrochloride chloride is precipitated, covered by suction filtering and dried in vacuo and it then melts at 190°-191° C. (analytically pure). (GC/MS of base: 100°-250° C. (20° C./min) RT=19.94, m/e 357.25.

The NMR spectrum of the $^{13}C$ of this compound and its percentage analysis are given in the attached tables 2 and 3.

EXAMPLE 17

Preparation of
1-(2-benzo(b)thiophenyl)-3,5-(dimethyl-1-piperidino)-1-cyclohexane (compound 6)

The Grignard reagent resulting from the action of 10.4 g (0.04 mole) of 2-iodobenzo(b)thiophene on 1,5 g (0.06 mole) of magnesium turnings is prepared in 50 ml of anhydrous ether. To it are slowly added 4.5 g (0.02 mole of synthon V of example 5 dissolved in 20 ml of anhydrous ether. Stirring takes place for 16 h at reflux, the complex is decomposed by a cold saturated $NH_4Cl$ solution and then, after decanting, extraction takes place with ether (3×50 ml). The combined ethereal phases are extracted by an aqueous 20% HCl solution (3×50 ml). The acid waters are neutralized by $NH_4OH$ and extracted with ether (2×79 ml). The combined ethers, after drying on $Na_2SO_4$, undergo vacuum evaporation to give 5 g of a yellowish solid residue. The latter is crystallized twice in methanol to give 4 g of compound 6 in the form of white crystals (61%) melting at 98°-99° C. By bubbling the gaseous HCl into the ethereal solution of this compound, its white solid hydrochloride is precipitated and following recovery by suction filtering and vacuum drying melts at 192°-193° C. (analytically pure). (GC/MS of base: 70°-250° C. (15° C./min) RT=17.62 min, m/e 327.25).

The NMR spectrum of the $^{13}C$ of this compound and its percentage analysis are given in the attached tables 2 and 3.

EXAMPLE 18

Preparation of
1-(2-benzo(b)thiophenyl)-4-(methyl-1-piperidino)-1-cyclohexane (compound 7)

The Grignard reagent resulting from the action of 10.4 g (0.04 mole) of 2-iodobenzo(b)thiophene on 1.5 g (0.06 mole) of magnesium turnings is prepared in 70 ml of anhydrous ether. To it are slowly added 4.3 g (0.02 mole) of synthon IX of example 9 dissolved in 50 ml of anhydrous ether. Stirring takes place for 16 h at reflux and the complex is decomposed by a cold saturated $NH_4Cl$ solution and then, after decanting, extraction takes place with ether (3×100 ml). The combined ethereal phases are extracted by an aqueous 20% HCl solution (3×100 ml). The acid waters are neutralized by $NH_4OH$, extracted with ether (2×100 ml) and with methylene chloride (2×100 ml). The combined organic phases, after drying on $Na_2SO_4$, undergo vacuum evaporation to give 4 g of a yellowish solid residue. The latter undergoes chromatography on Merck alumina (activity 2-3) in a mixture of ether and hexane (10/90 v/v) to give 3.7 g of compound 7 in the form of a white solid (59%) melting at 84°-85° C. By bubbling gaseous HCl into the ethereal solution of this compound, its white solid hydrochloride is precipitated and, when recovered by suction filtering and vacuum drying, melts at 190°-191° C. (analytically pure). (GC/MS of base: 70°-250° C. (15° C./min, RT=18.52 min, m/e 313.25).

The NMR spectrum of the $^{13}C$ of this compound and its percentage analysis are given in the attached tables 2 and 3.

EXAMPLE 19

Preparation of
1-(2-benzo(b)thiophenyl)-1-(1-diethylamino)-1-cyclohexane (compound 8)

In 150 ml of anhydrous ether is prepared the Grignard reagent resulting from the action of 17.3 g (0.066 mole) of 2-iodobenzo(b)thiophene on 1.7 g (0.07 mole) of magnesium turnings. To it are slowly added 6 g (0.033 mole) of synthon VIII of example 8 dissolved in 50 ml of anhydrous ether. Stirring takes place for 16 h at reflux, the complex is decomposed by a cold saturated NH$_4$Cl solution and then, after decanting, extraction takes place with ether (3×100 ml). The combined ethereal phases are extracted by an aqueous 20% HCl solution (3×100 ml). The acid waters are neutralized by NH$_4$OH, extracted with ether (3×100 ml) and the combined ethers, after drying on NA$_2$SO$_4$, undergo vacuum evaporation to give 6 g of a yellowish solid residue. The latter undergoes chromatography on Merck alumina (activity 2-3) in petroleum ether to give 5.4 g of compound 8 in the form of a colourless oil (58%). By bubbling gaseous HCl into the ethereal solution of said compound, its white solid hydrochloride is precipitated and after recovery by suction filtering and vacuum drying melts at 160°–161° C. (analytically pure). (GC/MS of base: 100°–250° C. (20° C./min, RT=9.58 min, m/e 287.15).

The NMR spectrum of the $^{13}$C of this compound and its percentage analysis are given in the attached tables 2 and 3.

EXAMPLE 20

Preparation of
1-(2-benzo(b)thiophenyl)-3-(hydroxymethyl-1-piperidino)-1-cyclohexane (compound 9)

The Grignard reagent resulting from the action of 12.5 g (0.048 mole) of 2-iodobenzo(b)thiophene on 1.7 g (0.07 mole) of magnesium turnings is prepared in 100 ml of anhydrous ether. To it are slowly added 5.4 g (0.024 mole) of synthon IV of example 4 dissolved in 50 ml of anhydrous ether. Stirring takes place for 16 h at reflux and the complex is decomposed by a cold saturated NH$_4$Cl solution and then, after decanting, the waters are extracted with ether (3×100 ml). The combined ethereal phases are extracted by an aqueous 20% HCl solution (2×100 ml). The acid waters are neutralized by 20% NH$_4$OH and extracted with ether (3×70 ml). After drying on Na$_2$SO$_4$, the combined ethers undergo vacuum evaporation to give 6 g of a yellowish oily residue. The latter undergoes chromatography on Merck alumina, (activity 2-3) in a mixture of ether and petroleum ether (90/10 v/v) to give 5 g (63%) of compound 9 in the form of a clear yellow oil. The latter slowly transforms into colourless crystals melting at 102°–103° C. By bubbling gaseous HCl into the ethereal solution of this compound, its solid white hydrochloride is precipitated and, after recovery by suction filtering and vacuum drying, melts at 188°–189° C. (analytically pure). (GC/MS of base: 50°–250° C. (20° C./min, RT=17.28 min, m/e 329.15).

The NMR spectrum of the $^{13}$C of this compound and its percentage analysis are given in the attached tables 2 and 3.

EXAMPLE 21

Preparation of
1-(2-benzo(b)thiophenyl)-1-(3-bromomethyl-1-piperidino)-cyclohexane (compound 10)

To 5.7 g (0.017 mole) of compound 9 of example 20 and 5 ml of methylene chloride are very slowly added (with evacuation or trapping for acid gases) and accompanied by stirring, 3.6 g (0.017 mole) of thionyl bromide dissolved in 2 ml of methylene chloride. Stirring takes place for one night at ambient temperature and the solvent is then evaporated in vacuo. The residue obtained is taken up in ether and washed with 10% HCl (2×200 ml). The aqueous phase is neutralized by 20% NH$_4$OH, extracted with ether (2×70 ml) and then with methylene chloride (70 ml). After combining and drying on Na$_2$SO$_4$, the organic phases are evaporated in vacuo to give 3 g of a brownish oily residue. The latter is purified by flash chromatography on silica in petroleum ether to give 2.7 g (41%) of compound 10 in the form of a colourless oil. By bubbling gaseous HCl into the ethereal solution of the base, its white solid hydrochloride is precipitated and after recovery by suction filtering and vacuum drying melts at 178°–179° C. (analytically pure). (GC/MS of base: 100°–250° C. (20° C./min, RT=16.42 min, m/e 391.5 and 393.05).

The NMR spectrum of the $^{13}$C of this compound and its percentage analysis are given in the attached tables 2 and 3.

EXAMPLE 22

Preparation of
1-(2-benzo(b)thiophenyl)-1-(3-iodomethyl-1-piperidino)-cyclohexane (compound 11)

To 2 g (0.006 mole) of compound 9 of example 20 and 10 ml of methylene chloride are slowly added accompanied by stirring and in a nitrogen atmosphere, 4.86 g (0.024 mole) of trimethyl silane iodide. Accompanied by stirring, the mixture is heated to 40° C. for 24 h, cooled and poured into a cold sodium disulphite solution and then extracted with methylene chloride (3×30 ml). The organic phase is dried on Na$_2$SO$_4$ and evaporated in vacuo to give 1.2 g of brownish oily residue. The latter is purified by chromatography on Merck alumina (activity 2-3) in a mixture of petroleum ether and ether (90/10 v/v) to give 0.7 g (18%) of compound 11 in the form of a clear oil. By bubbling gaseous HCl into the ethereal solution of this compound, its white solid hydrochloride is precipitated and, after suction filtering and vacuum drying, melts at 155°–156° C. (analytically pure). (GC/MS of base: 100°–250° C. (20° C./min, RT=19.07 min, m/e 439).

The NMR spectrum of the $^{13}$C of this compound and its percentage analysis are given in the attached tables 2 and 3.

EXAMPLE 23

Preparation of
1-(2-benzo(b)thiophenyl)-1-(3-chloromethyl-1-piperidino)-cyclohexane (compound 12)

To 3 g (0.009 mole) of compound 9 of example 20 and 5 ml of methylene chloride are very slowly added (accompanied by evacuation or trapping for the acid gases) and accompanied by stirring, 1.9 g (0.009 mole) of thionyl chloride dissolved in 2 ml of methylene chloride. Stirring takes place for 6 h at 60° C. and then, after cooling, the medium is poured into a Na₂CO₃ solution. After stirring for 15 min extraction takes place with methylene chloride (3×20 ml), followed by drying on Na₂SO₄ and vacuum evaporation of the solvent to give 2 g of a brownish oily residue. The latter is purified by flash chromatography on silica in petroleum ether and ether (90/10 v/v) to give 1 g (32%) of compound 12 in the form of colourless oil. By bubbling gaseous HCl into the ethereal solution of this compound, its white solid hydrochloride is precipitated and which, recovered by suction filtering and vacuum drying, melts at 182°-183° C. (analytically pure). (GC/MS of base: 100°-250° C. (20° C./min, RT=29 min, m/e 347.25).

The NMR spectrum of the $^{13}$C of this compound and its percentage analysis are given in the attached tables 2 and 3.

EXAMPLE 24

Preparation of
1-(2-benzo(b)thiophenyl)-r-1-(3,5-dimethyl-1-piperidino)-4-c-methyl-cyclohexane (compound 13)

The Grignard reagent resulting from the action of 15 g (0.06 mole) of 2-iodobenzo(b)thiophene on 1.7 g (0.07 mole) of magnesium turnings is prepared in 150 ml of anhydrous ether. To it are slowly added 6.75 g (0.03 mole) of synthon X of example 10 dissolved in 50 ml of anhydrous ether. Stirring takes place for 16 h at reflux, the complex is decomposed by a cold saturated NH₄Cl solution and then, after decanting, extraction takes place with ether (3×100 ml). The combined ethereal phases are extracted by an aqueous 20% HCl solution (3×100 ml). The acid waters are neutralized by NH₄OH, extracted with ether (2×70 ml) and then with methylene chloride (2×70 ml). The combined organic phases, after drying on Na₂SO₄, are evaporated in vacuo to give 6 g of an oily residue. Following flash chromatography on silica in petroleum ether, the latter gives 5.4 g (53%) of compound 13 in the form of a white solid melting at 115°-116° C. By bubbling gaseous HCl into the ethereal solution of this compound, its white solid hydrochloride is precipitated and, after recovery by suction filtering and vacuum drying, it melts at 198°-199° C. (analytically pure). (GC/MS of base: 100°-250° C. (20° C./min, RT=10.90 min, m/e 341.15). The NMR spectrum of the $^{13}$C of this compound and its percentage analysis are given in the attached tables 2 and 3.

EXAMPLE 25

Preparation of
1-(2-benzo(b)furanyl)-1-r-(3,5-dimethyl-1t-piperidino)-3-methyl-cyclohexane (compound 14)

In 100 ml of anhydrous ether is prepared the Grignard reagent resulting from the action of 10.4 g (0.04 mole) of 2-iodobenzo(b)furan on 1.2 g (0.05 mole) of magnesium turnings. To it are slowly added 5 g (0.02 mole) of synthon XI of example 11 dissolved in 50 ml of anhydrous ether. Stirring takes place for 16 h at reflux. The complex is decomposed by a cold saturated NH₄Cl solution and then, after decanting, is extracted with ether (3×100 ml). The combined ethereal phases are extracted by a 20% aqueous HCl solution (3×100 ml). The acid waters are neutralized by NH₄OH, extracted with ether (2×100 ml) and then with methylene chloride (2×100 ml). The combined organic phases, after drying on Na₂SO₄, undergo vacuum evaporation to give 3.1 g of an oily residue. Following flash chromatography on silica in petroleum ether, the latter gives 2.7 g (41.5%) of compound 14 melting at 92°-93° C. By bubbling gaseous HCl into the ethereal solution of this compound, its white solid hydrochloride is precipitated and, after recovery by suction filtering and vacuum drying, it melts at 185°-186° C. (analytically pure). (GC/MS of base: 100°-250° C. (20° C./min, RT=8.9 min, m/e 325.15).

The NMR spectrum of the $^{13}$C of this compound and its percentage analysis are given in the attached tables 2 and 3.

EXAMPLE 26

Preparation of
1-(2-benzo(b)thiophenyl)-1-(3-hydroxymethyl-1-piperidino)-cyclohexane acetate (compound 15)

Stirring takes place for 24 h at 50° C. of 3 g (0.009 mole) of compound 9 with 1.8 g (0.018 mole) of acetic anhydride and 1.4 g (0.018 mole) of pyridine. The mixture is then poured into iced water and extracted with ether (3×50 ml). The dried ethers (Na₂SO₄) are evaporated under reduced pressure to give 2 g of oily residue. By silica column chromatography in petroleum ether 1.7 g of compound 15 is collected in the form of a colourless oil (51%). By bubbling gaseous HCl into the ethereal solution of the compound, its solid white hydrochloride is precipitated and, after recovery by suction filtering and vacuum drying, melts at 145°-147° C. (analytically pure). (GC/MS of base: 70°-250° C. (15° C./min RT=21.09 min, m/e 371.20).

The NMR spectrum of the $^{13}$C of this compound and its percentage analysis are given in the attached tables 2 and 3.

EXAMPLE 27

Preparation of
1-(2-naphthyl)-1-(1-piperidino)cyclohexane (compound 16)

The Grignard reagent resulting from the action of 5 g (0.024 mole) of 2-bromonaphthalene on 0.6 g of magnesium turnings is prepared in 30 ml of anhydrous ether. To it are slowly added 3 g (0.016 mole) of synthon I of example 1 dissolved in 30 ml of anhydrous ether. Stirring takes place for 16 h at reflux and the complex is decomposed by a cold saturated NH₄Cl solution and then, after decanting, extraction takes place with ether (3×30 ml). The combined ethereal phases are extracted by an aqueous 15% HCl solution (3×30 ml). The acid waters are neutralized by NH₄CH and extracted with ether (3×30 ml). The combined ethers, after drying on Na₂SO₄, are vacuum evaporated to give a yellowish solid residue of 2 g. Chromatography on Merck alumina (activity 2-3) in petroleum ether supplies 1.3 g (28%) of compound 16 in the form of white crystals melting at 80°-82° C. By bubbling gaseous HCl into the ethereal solution of the base, its white solid hydrochloride is precipitated and, after recovery by suction filtering and vacuum drying, melts at 155°-156° C. (analytically pure). (GC/MS of base: 100°-250° C. (20° C./min RT=10.38 min, m/e 293.20).

The NMR spectrum of the $^{13}$C of this compound and its percentage analysis are given in the attached tables 2 and 3.

EXAMPLE 28

Preparation of
1-(1-naphthyl)1-(1-piperidino)cyclohexane (compound 17)

The Grignard reagent resulting from the action of 11.3 g (0.036 mole) of 1-bromonaphthalene on 1.3 g of magnesium turnings, is prepared in 50 ml of anhydrous ether. To it are slowly added 3.5 g (0.018 mole) of synthon I of example 1 dissolved in 20 ml of anhydrous ether. Stirring takes place for 16 h at reflux, the complex is decomposed by a cold saturated NH$_4$Cl solution and then, after decanting, extraction takes place with ether (3×20 ml). The combined ethereal phases are extracted by an aqueous 15% HCl solution (3×20 ml). The acid waters are neutralized by NH$_4$OH, extracted with ether (3×20 ml) and the combined ethers, after drying on Na$_2$SO$_4$, are evaporated in vacuo to give 4 g of a yellowish oily residue. Chromatography on Merck alumina (activity 2-3) in petroleum ether and ether (90/10 v/v) gives 3.3 g of compound 17 in the form of a colourless oil (62%). By bubbling gaseous HCl into the ethereal solution of the base, its white solid hydrochloride is precipitated and, after recovery by suction filtering and vacuum drying, melts at 190°-191° C. (analytically pure). (GC/MS of base: 1000°-250° C. (20° C./min RT=9.86 min, m/e 293.20).

The NMR spectrum of the $^{13}$C of this compound and its percentage analysis are given in the attached tables 2 and 3.

EXAMPLE 29

Preparation of
1-(2-benzo(b)thiophenyl)-t-ter-butyl-4-r-(1-piperidino)-1 cyclohexane (compound 18) and
1-(2-benzo(b)thiophenyl)-c-ter-butyl-4-r-(1-piperidino)-1 cyclohexane (compound 19)

A) The Grignard reagent resulting from the action of 27 g (0.096 mole) of 2-iodobenzo(b)thiophene on 3.1 g (0.13 mole) of magnesium turnings is prepared in 150 ml of anhydrous ether. To it are added 10.7 g (0.069 mole) of ter butyl 4 cyclohexanone dissolved in 150 ml of anhydrous ether. Stirring takes place for 16 h at reflux, the complex is decomposed by a cold saturated NH$_4$Cl solution and then, after decanting, the waters are extracted with ether (2×100 ml) and methylene chloride (2×100 ml). The organic phases, after drying on Na$_2$SO$_4$, are evaporated in vacuo to give 18 g of crude alcohols. By crystallization in hexane, 16.5 g (82.5%) of white powder are isolated. (IR, GC/MS: 100°-250° C. (20° C./min) RT=10.96 min, RT=11.72 min, m/e 288.25). The following reaction takes place by carbocation, so that the alcohols are not otherwise purified.

B) At −15° C. a highly stirred suspension containing 6.77 g (0.104 mole) of sodium azide, 86.5 g (0.52 mole) of trichloroacetic acid and 100 ml of chloroform is prepared. To it is rapidly added, dissolved in 100 ml of chloroform and at the same temperature, 15 g (0.052 mole) of the previously obtained alcohols. The stirring and temperature are maintained for 3 h (or until the alcohols disappear) at −10° C., followed by the cold neutralization by 20% NH$_4$OH, decanting, and extraction of the aqueous phase with methylene chloride (3×60 ml). The collected organic phases are washed to a neutral pH. After drying on Na$_2$SO$_4$ and vacuum evaporation an oily residue is recovered weighing 15 g, which essentially contains an unsaturated derivative (highly minority) and two epimeric azides (IR 2150 cm$^{-1}$, GC/MS: 100°-250° C. (20° C./min) RT=10.72 min, RT=11.28 min, m/e 316.25), which, taking account of their relative instability, are not otherwise purified.

C) The 15 g of mixture of the two previously obtained azides is dissolved in 100 ml of isopropanol and heated at 65° C. for 30 min. To it is added portionwise Raney nickel (whilst maintaining the temperature) until the evolution of gas stops. It is then heated to 70° C. for 15 min, cooled to ambient temperature, diluted with water and filtered on celite. The aqueous phase collected is extracted with methylene chloride (3×100 ml), dried on MgSO$_4$ and evaporated in vacuo to give 9.5 g of a brown oily residue essentially containing 2 epimeric primary amines (IR disappearance N$_3$, GC/MS: 100°-250° C. (10° C./min), RT=9.02 min, RT=9.98 min, m/e 287.15).

D) 7 g of the aforementioned amines are dissolved in 100 ml of ethanol containing 5.61 g (0.024 mole) of 1,5-dibromopentane and 6.7 g (0.049 mole) of K$_2$CO$_3$. The highly stirred mixture is refluxed for 48 h and then cooled to ambient temperature. After filtering and evaporating the solvent, 150 ml of 10% HCl are added to the residue and extraction takes place with ether (3×50 ml). The acid waters neutralized by 20% NH$_4$OH are in turn extracted with ether (3×100 ml). After drying on Na$_2$CO$_3$, the ethers are evaporated in vacuo to give a white solid of 5 g. The mixture obtained undergoes chromatography on a Merck alumina column (activity 2-3). The petroleum ether makes it possible to collect 2.4 g of the solid white compound 19 melting at 139°-140° C. and a mixture of petroleum ether and ether (70/30 v/v) makes it possible to collect 1.6 g of solid white compound 18 melting at 148°-149° C. (24% overall yield based on the ketone). By bubbling gaseous HCl into the ethereal solution of the compounds, their solid white hydrochlorides are precipitated and, after recovery by suction filtering and vacuum drying melt respectively at 146°-147° C. (no. 19) and 208°-209° C. (no. 18) (analytically pure). (GC/MS of bases: 100°-250° C. (15° C./min) no. 18 RT=13.40 min, m/e=313.25; no. 19 RT=14.88 min, m/e 313.25).

The NMR spectrum of the $^{13}$C of this compound and its percentage analysis are given in the attached tables 2 and 3.

EXAMPLE 30

Preparation of
1-(2-benzo(b)thiophenyl)-t-methyl-4-r-(1-piperidino)-cyclohexane (compound 20) and
1-(2-benzo(b)thiophenyl)-c-methyl-4-r-(1-piperidino)-cyclohexane (compound 21)

A) The Grignard reagent resulting from the action of 29 g (0.112 mole) of 2-iodobenzo(b)thiophene on 3.1 g (0.13 mole) of magnesium turnings is prepared in 150 ml of anhydrous ether. To it are added 9.1 g (0.018 mole) of 4-methyl-cyclohexanone dissolved in 150 ml of anhydrous ether. Stirring takes place for 12 h at reflux, the complex is decomposed by a cold saturated NH$_4$Cl solution and then, after decanting, the waters are extracted with ether (2×150 ml) and then with methylene chloride (2×150 ml). The organic phases, dried on Na$_2$SO$_4$, are evaporated in vacuo to give 17 g of a pale yellow oil essentially containing two epimeric alcohols. (IR, GC/MS: 100°-250° C. (20° C./min, RT=14.28 min, m/e 246.10; RT=14.50 min, m/e 246.10). The following reaction (B) takes place by carbocation, so that the alcohols are not otherwise purified.

B) At −20° C. a suspension containing 7.9 g (0.12 mole) of sodium azide, 69.5 g (0.6 mole) of trichloroacetic acid and 250 ml of chloroform is prepared and strongly stirred. To it are rapidly added, dissolved in 150 ml of chloroform and at the same temperature, 15 g of previously obtained crude alcohols. The stirring and temperature are maintained for 3 h or until the alcohols disappear. The pasty medium obtained is poured into a cold $Na_2CO_3$ solution. After decanting, extraction takes place with chloroform (2×100 ml) and the collected organic phases are washed to a neutral pH. After drying on $Na_2SO_4$ and evaporation in vacuo an oily residue weighing 16 g is recovered and which essentially contains an unsaturated derivative (highly minority) and two epimeric azides (IR) which, taking account of their relative instability, are not otherwise purified.

C) 15 g of the mixture of the two previously obtained azides are dissolved in 150 ml of isopropanol and heated at 65° C. for 30 min. Raney nickel is added portionwise, whilst maintaining the temperature, until the gaseous evolution stops. Heating then takes place to 70° C. for 15 min, cooling to ambient temperature and filtering on celite. The filtrate, diluted with methylene chloride, is washed with water, dried on $Na_2CO_3$ and evaporated in vacuo to finally give an oily residue. The latter is dissolved in 10% HCl and washed with ether (2×200 ml), the aqueous phase being neutralized by 20% $NH_4OH$ and extracted with ether (2×200 ml). After drying on $Na_2CO_3$ and evaporation in vacuo, an oily residue weighing 9 g is obtained, which essentially contains two epimeric primary amines (IR).

D) 7 g of the mixture of amines referred to hereinbefore are dissolved in 100 ml of acetonitrile containing 6.6 g of 1,5-dibromopentane (0.028 mole) and 7.9 g (0.057 mole) of $K_2CO_3$. The highly stirred mixture is refluxed for 48 h and then cooled to ambient temperature. After filtering addition takes place of 100 ml of 20% HCl and extraction with ether (2×50 ml). The two acids, neutralized by $NH_4OH$, are in turn extracted with ether (3×50 ml). After drying on $Na_2CO_3$, said ethers are evaporated in vacuo to give 7.1 g of red oily residue. The latter undergoes chromatography on Merck alumina (activity 2-3). The petroleum ether elutes a first 4 g fraction of white crystals of compound 2 melting at 113°–114° C. and a mixture of petroleum ether and ether (50/50 v/v) elutes a second 2.3 g white crystal fraction of compound 20 melting at 120°–121° C. (38.6%) overall yield based on the ketone. By bubbling gaseous HCl into the ethereal solution of the compounds, their solid white hydrochlorides are precipitated and, after recovery by suction filtering and drying in vacuo, they respectively melt at 195°–196° C. (no. 21) and 209°–210° C. (no. 20) (analytically pure). (GC/MS of bases: 100°–250° C. (20° C./min, no. 20: RT=10.56 min, m/e 313.15); no. 21: RT=10.86 min, m/e 313.15).

The NMR spectrum of the $^{13}C$ of this compound and its percentage analysis are given in the attached tables 2 and 3.

EXAMPLE 31

Preparation of
1-(2-benzo(b)thiophenyl)-c-methyl-3-r-(1-piperidino)-cyclohexane (compound 22) and
1-(2-benzo(b)thiophenyl)-t-methyl-3-r-(1-piperidino)-cyclohexane (compound 23)

A) The Grignard reagent resulting from the action of 15.6 g (0.06 mole) of 2-iodobenzo(b)thiophene on 1.9 g (0.08 mole) of magnesium turnings is prepared in 50 ml of anhydrous ether. To it are added 5.6 g (0.05 mole) of 3-methyl-cyclohexanone dissolved in 50 ml of anhydrous ether. Stirring takes place for 12 h at reflux, the complex is decomposed by a cold saturated $NH_4Cl$ solution and then, after decanting, the waters are extracted with ether (2×100 ml) and then with methylene chloride (2×100 ml). The organic phases dried on $Na_2SO_4$ are evaporated in vacuo to give a yellow oil which, after filtering on a Merck alumina column (activity 2-3) in petroleum ether-ether (50/50 v/v) supplies 9 g of viscous clear oil essentially containing two epimeric alcohols. (IR, (GC/MS: 100°–250° C. (20° C./min, RT=12.20 min; m/e 246.20); RT=12.42 min, m/e 246.20). The following reaction takes place by carbocation, so that the alcohols are not otherwise purified.

B) At −15° C. preparation takes place of a suspension containing 4.23 g (0.065 mole) of sodium azide, 7.42 g (0.065 mole) of trifluoroacetic acid and 80 ml of chloroform, accompanied by strong stirring. To it are rapidly added, dissolved in 80 ml of chloroform and at the same temperature, 8 g of previously obtained crude alcohols. The stirring and temperature are maintained for 3 h or until the alcohols disappear. Neutralization takes place cold with 20% $NH_4OH$, followed by decanting, extraction with methylene chloride (3×75 ml) and the washing of the collected organic phases to a neutral pH. After drying on $Na_2SO_4$ and vacuum evaporation, an oily residue weighing 7.8 g is collected, which essentially contains an unsaturated derivative (highly minority) and two epimeric azides (IR, GC/MS: 70°–250° C. (15° C./min) RT=12.78 min, RT=12.90 min, m/e 271.20) which, bearing in mind their relative instability, are not otherwise purified.

C) 7 g of the mixture of the two previously obtained azides are dissolved in 80 ml of isopropanol and heated at 65° C. for 30 min. Raney nickel is added thereto in portions (whilst maintaining the temperature) until gaseous evolution stops. Heating then takes place to 70° C. for 15 min, cooling to ambient temperature and filtering on celite. The filtrate, diluted with methylene chloride, is washed with water, dried on $Na_2CO_3$ and evaporated in vacuo and finally gives an oily residue. The latter, dissolved in 10% HCl, is washed with ether (2×100 ml), the aqueous phase is neutralized by 20% $NH_4OH$ and extracted with ether (2×100 ml). After drying on $Na_2CO_3$ and vacuum evaporation, an oily residue weighing 3.6 g is collected, which essentially contains two epimeric primary amines (IR, GC/MS: 100°–250° C. (20° C./min) RT=9.20 min, RT=9.60 min, m/e 245.20).

D) 3 g of the aforementioned mixture of amines are dissolved in 50 ml of acetonitrile containing 2.8 g of 1,5-dibromopentane (0.012 mole) and 3.3 g (0.024 mole) of $K_2CO_3$. The highly stirred mixture is refluxed for 48 h and then cooled to ambient temperature. After filtering, 100 ml of 10% HCl are added, followed by extraction with ether (2×30 ml). The acid waters, neutralized by NH₄OH, are in turn extracted with ether (3×70 ml). After drying on Na₂CO₃, these ethers are evaporated in vacuo to give 2.5 g of a reddish oily residue. The latter is chromatographed on a silica column. The petroleum ether elutes a first 1.2 g white crystal fraction of compound 23 melting at 80°-81° C. and an ether-petroleum ether mixture (50/50 v/v) elutes a second 1.1 g white crystal fraction of compound 22 melting at 83°-84° C. (22% overall yield based on the ketone). By bubbling gaseous HCl into the ethereal solution of the bases, their solid white hydrochlorides are precipitated and, when recovered by suction filtering and vacuum drying, respectively melt at 162°-163° C. (no. 22) and 165°-166° C. (no. 23) (analytically pure) (GC/MS of bases: 100°-250° C. (20° C./min no. 22 RT=12.26 min, m/e 313.25); no. 23 RT=12.62 min, m/e 313.25).

The NMR spectrum of the $^{13}$C of this compound and its percentage analysis are given in the attached tables 2 and 3.

EXAMPLE 32

Preparation of
1-(2-benzo(b)thiophenyl)-c-methyl-2-r-(1-piperidino)-cyclohexane (compound 24) and
1-(2-benzo(b)thiophenyl)-t-methyl-t-r-(1-piperidino)-cyclohexane (compound 25)

A) The Grignard reagent resulting from the action of 33 g (0.13 mole) of 2-iodobenzo(b)thiophene on 3.6 g (0.15 mole) of magnesium turnings is prepared in 100 ml of anhydrous ether. To it are added 9.52 g (0.085 mole) of 2-methyl-cyclohexanone dissolved in 100 ml of anhydrous ether. Stirring takes place for 12 h at reflux, the complex is decomposed by a cold saturated NH₄Cl solution and then, after decanting, the waters are extracted with ether (2×100 ml) and then with methylene chloride (2×100 ml). The organic phases dried on Na₂SO₄ are evaporated in vacuo to give 15 g of a yellowish oil essentially containing two epimeric alcohols (IR, GC/MS: 100°-250° C. (20° C./min) RT=7.60 min, m/e 246.20; RT=7.78 min, m/e 246.20). The following reaction takes place by carbocation, so that the alcohols are not otherwise purified.

B) At −15° C. preparation takes place of a suspension containing 10.5 g (0.16 mole) of sodium azide, 18.5 g (0.16 mole) of trifluoroacetic acid and 50 ml of chloroform and strong stirring takes place. To it are rapidly added, dissolved in 50 ml of chloroform and at the same temperature, 10 g of the previously obtained crude alcohols. The stirring and temperature are maintained for 3 h or until the alcohols disappear. Neutralization takes place cold with 20% NH₄OH, followed by decanting, extraction with methylene chloride (3×75 ml) and washing of the collected organic phases to a neutral pH. After drying on Na₂SO₄ and vacuum evaporation, 9.1 g of an oily residue are recovered essentially containing two unsaturated derivatives (highly minority) and two epimeric azides (IR, GC/MS: 100°-250° C. (20° C./min) RT=8.1 min, RT=8.22 min, m/e 271.15) which, bearing in mind their relative instability, are not otherwise purified.

C) 8 g of the mixture of the two previously obtained azides are dissolved in 80 ml of isopropanol and heated at 65° C. for 30 min. Raney nickel is added portionwise, whilst maintaining the temperature until the gaseous evolution stops. Heating then takes place to 75° C. for 15 min, followed by cooling to ambient temperature and filtering on celite. The filtrate, diluted with methylene chloride, is washed with water, dried on Na₂CO₃ and evaporated in vacuo, finally giving an oily residue. The latter is dissolved in 10% HCl and washed with ether (2×100 ml). The aqueous phase is neutralized by 20% NH₄OH and extracted with ether (2×100 ml). After drying on Na₂CO₃ and vacuum evaporation, an oily residue weighing 5 g is collected and which essentially contains two epimeric primary amines (IR, GC/MS: 100°-250° C. (20° C./min) RT=7.44 min, RT=7.84 min, m/e 245.20).

D) 3 g of the previously obtained mixture of amines are dissolved in 30 ml of acetonitrile containing 2.8 g of 1,5-dibromopentane (0.012 mole) and 3.3 g (0.024 mole) of K₂CO₃. The highly stirred mixture is refluxed for 48 h and then cooled to ambient temperature. After filtering, 100 ml of 10% HCl are added and extraction takes place with ether (2×30 ml). The acid waters, neutralized by NH₄OH, are in turn extracted with ether (3×70 ml). After drying on Na₂CO₃, said ethers are evaporated in vacuo to give 1.8 g of a reddish oily residue, which is chromatographed on a Merck alumina column (activity 2-3). The petroleum ether elutes a first fraction of 0.7 g of white crystals of compound 25 melting at 103°-104° C. and a mixture of petroleum ether and ether (90/10 v/v) elutes a second fraction of 0.7 g of white crystals of compound 24 melting at 105°-106° C. (10% overall yield based on the ketone). By bubbling gaseous HCl into the ethereal solution of the bases, their solid white hydrochlorides are precipitated and, when recovered by suction filtering and vacuum drying, respectively melt at 177°-178° C. (no. 24) and 124°-125° C. (no. 25) (analytically pure) (GC/MS of bases: 100°-250° C. (20° C./min) no. 24 RT=11.02 min, m/e 313.25; no. 25 RT=10.94 min, m/e 313.25).

The NMR spectrum of the $^{13}$C of this compound and its percentage analysis are given in the attached tables 2 and 3.

EXAMPLE 33

Preparation of
1-(2-benzo(b)thiophenyl)-1-(ol-4-piperidino)-cyclohexane (compound 26)

To 1 g (2.89 mmole) of compound 5 dissolved in 20 ml of acetone are added 10 ml of a 20% HCl solution. The mixture is refluxed until the starting product completely disappears (4 h-TLC). The acetone is evaporated under reduced pressure, the aqueous residue neutralized (20% NH₄OH) and extracted by CH₂Cl₂ (2×10 ml). After washing with water, drying on MgSO₄ and evaporation under reduced pressure of the organic phase, 0.8 g (88%) of the ketonic derivative is obtained (IR, GC/MS). Said 0.8 g (2.56 mmole) is dissolved in 20 ml of anhydrous THF to which are added 2.6 ml of a 1N BH₃ solution in THF. The mixture is stirred at ambient temperature until the ketonic derivative disappears (1 h, TLC, IR). The solution is hydrolyzed by a little water, the THF evaporated under reduced pressure and the residue taken up in 15 ml of CH₂Cl₂. The organic solution is washed with water, dried on MgSO₄, evaporated under reduced pressure and gives 0.6 g (84%) of alcohol melting at 111°-112° C. (analytically pure). The NMR spectrum of the $^{13}$C of said compound and its percentage analysis are given in the attached tables 2 and 3.

EXAMPLE 34

Inhibition Test of the Capture of $^3$H Dopamine by Striated Synaptosomes of the Rat This test is carried out according to the method used by Vignon and Lazdunski operating in the following way. Wistar rats weighing 200–250 g are killed by cervical dislocation. Their brains are rapidly removed and the striata are dissected on ice. the striata are then homogenized (10 backward and forward movements) with a Potter homogenizing agent in 50 volumes of Tris HCl 10 mM buffer at pH 7.4 and containing 0.32M of sucrose. The homogenate is then centrifuged at 1000 g for 10 min at 4° C. and then the supernatant obtained is recentrifuged at 10000 g for 20 min at 4° C. The resulting P2 deposits containing crude synaptosomes are then used without supplementary purification.

The deposits are taken up in a Ringer medium (mM:140 NaCl, 5 KCl, 2.6 CaCl$_2$, 1.3 MgSO$_4$ 10 Tris-HCl, pH=7.4)+200 $\mu$M of pargyline and equilibrated for 30 min at 30° C. The compound to be tested is preincubated at the desired concentration for 30 min at 30° C. in the presence of the P2 deposit to a final protein concentration of 0.15 to 0.20 mg/ml in the Ringer medium.

Tritiated dopamine (($^3$H)DA, Amersham) is then added to a concentration of 5 nM for 5 min at 30° C. and its capture is interrupted by filtering 150 $\mu$l of incubation medium on glass fibre filters GF/B (Whatman). The radioactivity retained by the filters is measured in a liquid scintillation counter with 3 ml of ACS (Amersham) as the scintillating agent. The non-specific capture is measured at 4° C. in parallel incubations and is then subtracted from the total capture measured at 30° C. The IC$_{50}$ is the concentration of compound inhibiting 50% of the specific capture obtained in the absence of an inhibitor.

The compounds to be tested are initially solubilized in water to a concentration of 1 mM and the other concentrations are obtained by successive dilutions of said mother solution in water.

The results obtained are given in the attached table 4. The table shows that the tested compounds are able, at a very low concentration, to inhibit the synaptosomal capture of dopamine.

EXAMPLE 35

Affinity of the Compounds for the Bonding Sites of the ($^3$H)BTCP on Striatal Membranes of Rat Brains The striata of rat brains rapidly dissected in ice are homogenized with an Ultraturax for 30 s (position 6) in 50 volumes of a 0.32 M sucrose solution buffered by Tris-HCl 10 mM at pH 7.4. The homogenate is centrifuged at 4° C. and 1000 g for 10 min, whilst the supernatant obtained is centrifuged at 40000 g at 4° C. for 30 min, the deposits obtained being taken up in 1 ml of buffer/striatum.

The affinity of the compounds for the dopamine recapture complex is determined by competition experiments on striatum membranes prepared as described hereinbefore. The radioactive ligand used is ($^3$H)BTCP (Service des Molécules Marquées du CEA, Saclay France) at 55Ci/mmol.

The membranes (final protein concentration 0.1 to 0.2 mg/ml are incubated in 1 ml of 50 mM sodium phosphate buffer, pH 7.4, in the presence of a fixed tritiated ligand concentration (0.2 nM) and increasing concentrations of the compound to be tested. After 90 min at 40° C., 3 aliquot portions of 250 $\mu$l are filtered in vacuo on glass fibre filters GF/B (Whatman). The non-specific bond is obtained in parallel experiments carried out in the presence of 10 $\mu$m unlabelled BTCP. It is subtracted from the total bond to obtain the specific bond. The compound concentration preventing 50% of the specific bond of the radioactive ligand (IC$_{50}$) reflects the affinity of the latter for the dopamine recapture complex in the nerve endings.

The results obtained are given in the attached table 4. These results show that the compounds according to the invention are very active as inhibitors of the recapture of dopamine by the nerve endings, because they inhibit in the same way at low concentrations (IC$_{50}$ approximately 1 nanomolar) both the recapture of dopamine and the fixing of ($^3$H)BTCP. There is an excellent correlation between the affinity of the compounds for the ($^3$H)BTCP site and their inhibiting capacity of the recapture of ($^3$H)DA(R=0.99; n=13; p<0.001). For comparison purposes, the table includes the results obtained with Nomifensine (known inhibitor of the recapture of DA), which is much less powerful in its effect than most of the tested compounds.

EXAMPLE 36

Affinity of the Compounds for the Bonding Sites of ($^3$H)TCP on Rat Brain Homogenates This test is used for measuring the affinities of the compounds for the PCP receptor by competition experiments on rat brain homogenates. The radioactive ligand used is ($^3$H)TCP at a specific activity of 62 Ci/mmole (Service des Molécules Marquées, CEA Saclay France).

The rat brains (without the cerebellum and the cerebral trunk) are homogenized with the Ultraturax in 20 volumes of Hepes-Tris 50 mM buffer at pH 7.7. After centrifuging for 30 min at 15000 g, the deposits are taken up in the same volume of buffer and recentrifuged under the same conditions. The final deposits are taken up in Hepes-Tris 50 mM buffer at pH 7.7, so as to obtain a protein concentration of 6 to 8 mg/ml.

The competition experiments are carried out by incubating the membranes for 30 min (final protein concentration 0.6 to 0.8 mg/ml) in 5 mM Hepes-Tris buffer medium at pH 7.7 and 25° C., in the presence of a fixed concentration of tritiated ligand (1 nM) and increasing concentrations of the compounds to be tested. Three 600 $\mu$L samples are then filtered on glass fibre filters GF/B pretreated by PEI (polyethyleneimine) at 0.1%. The filters are rinsed with 3×5 ml of Tris HCl 10 mM, NaCl 100 mM buffer and the radioactivity retained is measured in a liquid scintillation counter. The non-specific bond is obtained in the presence of 100 $\mu$M TCP. The IC$_{50}$ is the concentration of the compound inhibiting 50% of the specific bond of the radioactive ligand.

The results obtained are given in the attached table 4. It can be seen that all the tested compounds have a very low affinity for the PCP receptor (or even no affinity) and must consequently have little psychotomimetic activity linked with the interaction of the molecules with said receptor. However, there is a very significant selectivity factor for the dopamine recapture complex compared with the PCP receptor. Thus, compounds 21 and 3 give very good results.

EXAMPLE 37

Measure of the Noradrenaline Capture.

The capture of tritiated noradrenaline (40 Ci/mmole) is evaluated on the basis of crude synaptosomal preparations of rat hypothalamus (Sprague-Dawley mâle, 200–300 g, Charles River, St Aubin lès Elbeuf, France).

The animals are sacrificed by decapitation and the brains rapidly removed. The hypothalami, dissected at 0°–4° C., are homogenized in 10 volumes (weight/volume) of previously cooled 0.32M saccharose by means of a Potter Elvejhem homogenizer (clearance 80–130 μm, 800 rpm). The cell debris and nuclear material are eliminated by centrifuging (1000 g, 10 min, 4° C.). The supernatant constitutes the crude synaptosomal fraction. Aliquot portions (50 μl) of synaptosomal preparation are preincubated for 5 minutes at 37° C. in the presence of 20 μM pargyline and increasing concentrations of the compounds to be tested in 960 μl of a glucose-enriched Krebs-Ringer medium, (composition in mM: NaCl 103, $CaCl_2$ 1, $MgCl_2$ 1, $KH_2PO_4$ 1, $NaHCO_3$ 27, ascorbic acid 0.1 and glucose 5.4). Following said preincubation, the tritiated noradrenaline (final concentration 50 nM) is added in a volume of 40 μl and incubation is continued at 37° C. for 10 min. The reaction is stopped by diluting with 2 ml of iced medium and centrifuging (7000 g, 10 min, 4° C.). After washing the centrifuging deposits in 1 ml of iced medium, the sample is again centrifuged under the same conditions. The deposits obtained are resuspended in 250 μl of distilled water by sonication (Sonotrode TC 4 C). 100 μl of this suspension are used for measuring the radioactivity by liquid scintillation (SL 2000, Kontron Intertechniques, Trappes, France) and 50 μl for the determination of the protein levels (according to the method of Lowry et al).

The non-specific capture is studied simultaneously at 0° C. in the presence of different concentrations of the compound. The specific capture (total capture at 0° C.) is expressed in fentomoles/mg of proteins.

For each studied concentration the measurement was duplicated, 3 to 5 experiments being carried out on different days (different synaptosomal preparations). For each compound at least 4 concentrations were studied, normally between $10^{-9}$ and $10^6$M.

The results are given in the attached table 5.

EXAMPLE 38

Measuring the Locomotor Activity

The locomotor activity of Swiss mice (mâles CD1, 25–30 g, Charles River, St. Aubin lès Elbeuf, France) is measured in the Boissier-Simon actinometer (Apelex, Bagneux, France).

30 minutes after administering the compounds to be tested, (10 mg/kg, i.p.), the mice are introduced into individual Plexiglass cages (L=26 cm, l=20 cm, h=10 cm), which are equipped with two photoelectric cells 1 cm above the floor. Each cell is connected to an electromechanical counter. The locomotor activity corresponds to the number of rays traversed from the 20th to the 35th minute following introduction into the actinometry cages.

The results are given in table 5. These results show that compounds 2, 4 and 21 have a better effect than BTCP.

Tables 4 and 5 give in a comparative manner the results obtained with BTCP, Nomifensine and Haloperidol in the tests of examples 33 to 36.

The BTCP (2-benzo(b)thiophenyl)-(1-piperidino cyclohexane) was prepared in the following way. To the Grignard reagent prepared from 31.2 g (0.12 mole) of 2-iodobenzo(b)thiophene and 2.8 g of magnesium turnings in 100 ml of anhydrous ether was added dropwise at ambient temperature 12 g (0.063 mole) in 200 ml of anhydrous ether of synthon I of example 1. The solution was refluxed for 16 h and then cooled, after which it was poured into a saturated solution of $NH_4Cl$ and ice. After stirring for 30 minutes and decanting, extraction took place with ether (3×200 ml) followed by washing the ethers with 10% HCl (3×200 ml). The acid waters were neutralized by 20% $NH_4OH$, extracted with ether (3×200 ml) and the organic phase was washed with water to a neutral pH. After drying on $Na_2SO_4$ and evaporating under reduced pressure, 15.6 g of a white solid residue were obtained, which were crystallized twice in ethanol to give 14 g of colourless crystals (75%) melting at 80°–81° C. By bubbling gaseous HCl into the ethereal solution of the base, its solid white hydrochloride is precipitated and, after recovery by suction filtering and vacuum drying, it melts at 194°–195° C. (analytically pure) (GC/MS of base: 100°–250° C. (20° C./min) RT=10.36 min, m/e 299.20).

Nomifensine, i.e. 8-amino-2-methyl-4-phenyl-1,2,3,4-tetrahydroisoquinoline is a product known to act on the dopamine recapture system.

Haloperidol is a dopaminergic antagonist not acting on the recapture.

The results of tables 3 and 4 show that the amines according to the invention have a greater effect than Nomifensine and that their effect is not of the same type as that of Haloperidol. They also have a selectivity for the dopamine recapture complex which is better than that of BTCP.

The attached table 6 illustrates the results of the toxicity tests carried out on mice using the substituted amines of the invention at a dose of 100 mg/kg intraperitoneally.

EXAMPLE 39

Study of the Inhibition of Dopamine and Noradrenaline Recapture on Culture Neurons a) Primary Neuron Cultures

The black substance, a structure rich in dopaminergic cells, or the *locus coeruleus*, containing noradrenergic cellular bodies are dissected from 14 day rat embryos, which is the age at which the cells have finished their mitosis. The cells are mechanically dissociated in a medium without calcium or magnesium.

Seeding takes place in wells pretreated with D-polylysin at a density of 150000 cells/well in 400 μl of culture medium consisting of 70% M.E.M, 25% Hanks and 5% decomplemented Nu-serum, plus 3% D-glucose (1/20).

One-third of the culture medium is renewed every 3 days up to 9 days of in vitro development, when the cells appear to be mature. At this age, the culture still does not have glial cells.

b) Inhibition Test of the Recapture of Dopamine and Noradrenaline

The cells obtained in a) are preincubated for 15 min at ambient temperature with 400 μl of a buffer constituted by 5 mM Ringer disodium phosphate, pH 7.6, whose final concentration composition is: NaCl 120 mM;

CaCl$_2$ 2.6 mM; MgCl$_2$ 1.3 mM; KCl 5 mM; D-glucose 3 mM; Na$_2$HPO$_4$ 5 mM.

This is followed by the incubation for 10 min at 37° C. using the same buffer in the presence of ($^3$H)Da or ($^3$H)NA at a final concentration of 10$^{-8}$M and a 1/5 isotopic dilution and increasing concentrations of the compound to be tested in a final volume of 400 μl.

This is followed by rinsing three times rapidly with 750 μl of the same buffer at 4° C., which corresponds to a total time of 10 seconds. The cells are then recovered in twice 500 μl of 0.5N NaOH and their radioactivity is determined by counting with 4 ml of scintillating agent and 50 μl of glacial acetic acid. Prior to the rinsing operations, an aliquot portion of 100 μl of incubation medium was sampled and the free radioactivity thereon was determined by counting with 5 ml of scintillating agent.

An evaluation also took place of the passive diffusion of ($^3$H)DA or ($^3$H)NA in the cells in the presence of 10$^{-4}$M/l of Nomifensine or Desipramine, which are respectively dopamine and noradrenaline recapture inhibitors whilst following the same operating procedure without the compound to be tested.

The specific recapture of ($^3$H)DA or ($^3$H)NA is deduced from the difference between the total recapture and the passive diffusion for each of the tested compounds. The results obtained are given in the attached table 7. On the basis of these results it can be seen that compound 6 is a very powerful inhibitor of the recapture of dopamine, but also noradrenaline.

EXAMPLE 40

Study of the Inhibition of the In Vivo Fixing of ($^3$H)BTCP in Mice

This study made use of male Swiss mice weighing 20-25 g. The mice were placed in two groups and fed with standard laboratory food and water as required. There were 12 consecutive hours of artificial light cycles starting from 7 a.m. The experiments were carried out between 10 a.m. and 6 p.m. The in vivo fixing measurements of ($^3$H)BTCP were carried out in the manner described by Maurice et al, 1989, as follows.

The compound to be tested was subcutaneously injected into the mice in 100 μl of physiological solution for compounds 4 and 16 and in 100 μl of a 1:1 volume mixture of physiological solution and DMSO for compound 26. 60 min following this injection, ($^3$H)BTCP was injected into a vein of the tail at a dose of 5 μCi in 100 μl of a mixture of physiological solution and 5% ethanol. The mice were sacrificed 30 min after this injection. The striata of the brains were rapidly dissected and homogenized with an Ultraturax (IKA Verk), with the maximum setting for 20 s in 80 volumes of a Na$_2$HPO$_4$ 50 mM HCl buffer, at pH 7.4 and 4° C. Two aliquot portions of 1000 μl were filtered under reduced pressure on GF/B filters (Whatman), pretreated with 0.5% polyethyleneimine (Aldrich). The filters were then rinsed twice with 5 ml of 50 mM NaCl, 10 mM Tris-HCl buffer at pH 7.4 and 4° C. The fixed radioactivity remaining on the filters and the total radioactivity obtained from the two 200 μl aliquot homogenate portions are measured in 6 ml bottles containing 3.5 ml of ACS (Amersham) using an Excel 1410 liquid scintillation spectrophotometer (LKB). The nonspecific fixing is defined as the radioactivity present in each region after the pretreatment of the animals with BTCP (40 mg/kg in 100 μl of saline solution), injected subcutaneously 60 min following the injection of ($^3$H)BTCP. The results are expressed as fixed radioactivity/free radioactivity (B/F) ratios in which the free ($^3$H)BTCP level is estimated by subtracting the fixed radioactivity from the total radioactivity. At least 7 doses are used for determining the dose necessary for inhibiting 50% of the fixing of ($^3$H)BTCP (ID$_{50}$) with 5 mice per tested dose.

The results obtained are given in table 8.

TABLE 1

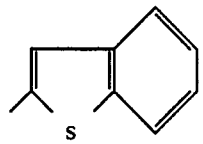

TABLE 1-continued
| COMPOUND | NR¹R² | Y | R³ | R⁴ | n | R⁵ |
|---|---|---|---|---|---|---|
| N° 3 | N(CH₂—CH₂—CH₃)₂ | CH | H | — | 0 | " |
| N° 4 | 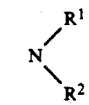 | CH | H | — | 0 | 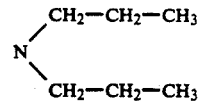 |
| N° 5 |  | CH | H | — | 0 | 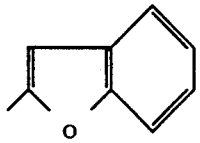 |
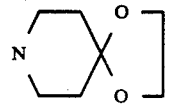
| N° 6 | 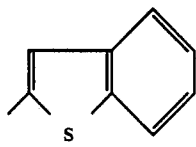 | CH | H | — | 0 | 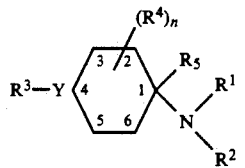 |
| N° 7 | 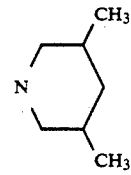 (4-CH₃) | CH | H | — | 0 | " |
| N° 8 | N(CH₂CH₃)₂ | CH | H | — | 0 | " |
| N° 9 | 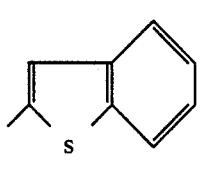 CH₂OH | CH | H | — | 0 | " |
| N° 10 | 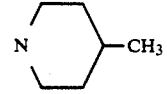 CH₂Br | CH | H | — | 0 | " |
| N° 11 | 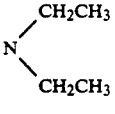 CH₂I | CH | H | — | 0 | " |

TABLE 1-continued

| COMPOUND | N(R¹)(R²) | Y | R³ | R⁴ | n | R⁵ |
|---|---|---|---|---|---|---|
| N° 12 | 3-(CH₂Cl)-piperidinyl | CH | H | — | 0 | benzothiophene-2-yl |
| N° 13 | 3,5-dimethylpiperidinyl | CH | c-CH₃ | — | 0 | " |
| N° 14 | 3,5-dimethylpiperidinyl | CH | H | t-CH₃ in 3 | 1 | benzofuran-2-yl |
| N° 15 | 3-(CH₂OOCCH₃)-piperidinyl | CH | H | — | 0 | " |
| N° 16 | piperidinyl | CH | H | — | 0 | naphthalen-2-yl |
| N° 17 | piperidinyl | CH | H | — | 0 | naphthalen-1-yl |
| N° 18 | piperidinyl | CH | t-terC₄H₉ | — | 0 | benzothiophene-2-yl |
| N° 19 | piperidinyl | CH | c-ter-C₄H₉ | — | 0 | " |
| N° 20 | piperidinyl | CH | t-CH₃ | — | 0 | " |
| N° 21 | piperidinyl | CH | c-CH₃ | — | 0 | " |

TABLE 1-continued

| COMPOUND | NR¹R² | Y | R³ | R⁴ | n | R⁵ |
|---|---|---|---|---|---|---|
| N° 22 | piperidine | CH | H | c-CH₃ in 3 | 1 | " |
| N° 23 | piperidine | CH | H | t-CH₃ in 3 | 1 | " |
| N° 24 | piperidine | CH | H | c-CH₃ in 2 | 1 | benzothiophene |
| N° 25 | piperidine | CH | H | t-CH₃ in 2 | 1 | benzothiophene |
| N° 26 | 4-hydroxypiperidine | CH | H | — | 0 | benzothiophene |

TABLE 2

NMR spectra of $^{13}$C: recorded in CDCl₃ at 20.147 MHz, in ppm based on TMS, in the base (*), or in the form of hydrochloride. The underlined values can be inverted.

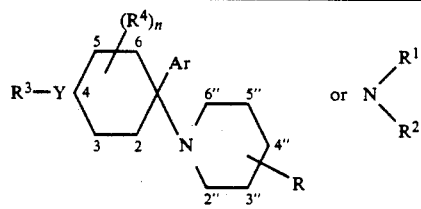

| Compound | n° 1* | n° 2 | n° 3 | n° 4 | n° 5 | n° 6 | n° 7 | n° 8 | n° 9ᵉ | n° 10 | n° 11 | n° 12 | n° 13 | n° 14 | n° 15 | n° 16 | n° 17 |
|---|---|---|---|---|---|---|---|---|---|---|---|---|---|---|---|---|---|
| 1 | 59.7 | 69.7 | 70.8 | 67.9 | 69.2 | 69.8 | 69.5 | 70.8 | 74.2 | 70.1 | 70.3 | 70.2 | 69.9 | 66.9 | 70.1 | 71.1 | 75.0 |
| 2 | 33.5 | 33.1 | 32.9 | 29.7 | 32.7 | 33.0 | 32.9 | 33.2 | 37.6 | 32.9 | 33.0 | 33.0 | 28.5 | 39.7 | 32.9 | 30.5 | 35.2 |
| 3 | 54.4 | 23.1 | 22.6 | 22.4 | 22.7 | 23.1 | 23.1 | 22.8 | 28.1 | 23.0 | 23.1 | 23.0 | 27. | 27.3 | 23.0 | 22.4 | 22.6 |
| 4 | — | 23.9 | 23.3 | 23.4 | 23.4 | 23.8 | 23.8 | 23.5 | 30.2 | 23.7 | 23.8 | 23.7 | 25.4 | 30.7 | 23.7 | 24.2 | 24.1 |
| 5 | 54.4 | 23.1 | 22.6 | 22.4 | 22.7 | 23.1 | 23.1 | 22.8 | 28.1 | 23.0 | 23.1 | 23.0 | 27.8 | 18.3 | 23.0 | 22.4 | 22.6 |
| 6 | 33.5 | 33.1 | 32.9 | 29.7 | 32.7 | 33.0 | 32.9 | 33.2 | 37.6 | 32.9 | 33.0 | 33.0 | 28.5 | 30.0 | 32.9 | 30.5 | 33.7 |
| 2″ | 47.3 | 53.0 | 51.5ᵇ | 47.3 | 44.7 | 52.5 | 47.1 | 44.2ᵈ | 54.6 | 50.3 | 52.2 | 49.3 | 52.2 | 53.4 | 49.0 | 47.0 | 49.0 |
| 3″ | 26.2 | 28.7 | 19.3ᵇ | 22.7 | 31.7 | 28.2 | 30.9 | 11.5ᵈ | 41.6 | 34.1 | 33.5 | 34.7 | 28.1 | 28.1 | 33.1 | 22.4 | 22.6 |
| 4″ | 24.7 | 31.0 | — | 21.8 | 63.8 | 39.9 | 29.6 | — | 29.2 | 27.7 | 29.3 | 26.1 | 39.8 | 39.9 | 25.4 | 21.9 | 21.9 |
| 5″ | 26.2 | 22.6 | 19.3ᵇ | 22.7 | 31.7 | 28.2 | 30.9 | 11.5ᵈ | 27.1 | 21.7 | 21.7 | 21.8 | 28.1 | 27.9 | 21.8 | 22.4 | 22.6 |

TABLE 2-continued

| 6" | 47.3 | 46.8 | 51.5[b] | 47.3 | 44.7 | 52.5 | 47.1 | 44.2[d] | 52.2 | 46.7 | 46.8 | <u>47.2</u> | 52.2 | <u>52.3</u> | 46.8 | 47.0 | <u>47.2</u> |
|---|---|---|---|---|---|---|---|---|---|---|---|---|---|---|---|---|---|
| $R^3$ or $R^4$ | 21.7 | — | — | — | — | — | — | — | — | — | — | — | 17.3 | 18.7 | — | — | — |
| R | — | 19.3 | — | — | — | 19.1 | 10.1 | 20.7 | 68.4 | 36.1 | 10.1 | <u>47.3</u> | 19.0 | 18.9 | 65.6 | — | — |
| CO | | | | | | | | | | | | | | 170.5 | | | |
| CH3 | 27.9[c] | — | 11.1[b] | — | 64.3[a] | — | — | — | — | — | — | — | — | 20.5 | — | — | — |

[a] $CH_2$—$CH_2$,
[b] propyl chain,
[c] N—$CH_3$,
[d] ethyl chain.
[e] DMSO $D_6$ NMR spectra of $^{13}C$: recorded in $CDCl_3$ at 20.147 MHz, in ppm based on TMS in the form of hydrochloride. The underlined values can be inverted.

| Compound | n° 18 | n° 19 | n° 20 | n° 21 | n° 22[a] | n° 23 | n° 24 | n° 25 | n° 26[c] |
|---|---|---|---|---|---|---|---|---|---|
| 1 | 69.4 | 68.9 | 69.4 | 69.9 | 69.8 | 68.7 | 73.2 | 75.3 | 60.4 |
| 2 | 33.2 | 31.6 | <u>32.8</u> | <u>28.6</u> | 44.5 | 39.2 | 35.6 | 37.1 | <u>35.7</u> |
| 3 | 24.1 | 21.7 | <u>31.3</u> | <u>27.6</u> | 27.5 | 27.3 | 30.3 | <u>31.8</u> | 22.3 |
| 4 | 45.4 | 41.8 | 30.3 | 25.5 | <u>33.1</u> | 30.5 | 18.8 | <u>22.4</u> | 25.9 |
| 5 | 24.1 | 21.7 | <u>31.3</u> | <u>27.6</u> | 22.8 | 18.6 | <u>22.4</u> | <u>22.4</u> | 22.3 |
| 6 | 33.2 | 31.6 | <u>32.8</u> | <u>28.6</u> | <u>31.7</u> | 33.0 | 26.9 | <u>30.5</u> | <u>35.7</u> |
| 2" | 47.5 | 48.0 | 47.5 | 47.3 | 47.5 | <u>47.3</u> | <u>49.3</u> | <u>49.5</u> | 43.1 |
| 3" | 22.9 | 22.3 | 22.9 | 22.9 | 22.8 | 22.6 | 22.7 | <u>22.7</u> | 35.8 |
| 4" | 22.3 | 21.9 | 22.2 | 22.4 | 22.3 | 22.1 | <u>22.3</u> | <u>22.4</u> | 68.4 |
| 5" | 22.9 | 22.3 | 22.9 | 22.9 | 22.8 | 22.6 | 22.7 | <u>22.7</u> | 35.8 |
| 6" | 47.5 | 48.0 | 47.5 | 47.3 | 47.5 | <u>47.4</u> | <u>47.3</u> | <u>49.0</u> | 43.1 |
| $R^3$ to $R^4$ | 31.9 | 32.6 | 21.1 | 17.4 | 20.5 | 18.6 | 16.0 | 18.1 | — |
| CH3 | 27.1[b] | 27.7[b] | — | — | — | — | — | — | — |

[a] DMSO,$D_6$.
[b] group tert-butyl
[c] base form

TABLE 3

| | | Percentage Analyses | | | | | | | |
|---|---|---|---|---|---|---|---|---|---|
| | | theoretical | | | | experimental | | | |
| n° | crude formula | C | H | N | Cl | C | H | N | Cl |
| 1 | $C_{23}H_{36}N_2SCl$ | 62.30 | 8.13 | 6.32 | 16.03 | 61.80 | 8.30 | 5.95 | 16.11 |
| 2 | $C_{20}H_{28}NSCl$ | 68.67 | 8.01 | 4.00 | 10.16 | 67.62 | 8.07 | 3.75 | 10.12 |
| 3 | $C_{20}H_{30}NSCl$ | 68.28 | 8.53 | 3.98 | 10.10 | 68.21 | 8.33 | 3.76 | 10.48 |
| 4 | $C_{19}H_{26}NOCl$ | 71.36 | 8.14 | 4.38 | 11.11 | 71.13 | 8.20 | 4.49 | 11.35 |
| 5 | $C_{21}H_{28}NOSCl$ | 64.04 | 7.11 | 3.56 | 9.02 | 63.56 | 7.09 | 3.48 | 8.92 |
| 6 | $C_{21}H_{30}NSCl$ | 69.71 | 7.75 | 3.87 | 9.82 | 69.60 | 8.04 | 3.58 | 9.65 |
| 7 | $C_{20}H_{28}NSCl$ | 68.67 | 8.01 | 4.00 | 10.16 | 68.99 | 7.91 | 4.10 | 10.00 |
| 8 | $C_{18}H_{26}NSCl$ | 66.77 | 8.04 | 4.33 | 10.97 | 66.55 | 7.99 | 4.21 | 11.06 |
| 9 | $C_{20}H_{22}NOSCl$ | 65.66 | 7.66 | 3.83 | 9.71 | 65.56 | 7.79 | 3.58 | 9.76 |
| 10 | $C_{20}H_{26}NSBr$ | 56.01 | 6.30 | 3.27 | | 55.90 | 6.38 | 3.14 | |
| 11 | $C_{20}H_{26}NSI$ | 50.47 | 5.68 | 2.94 | | 50.31 | 5.82 | 2.78 | |
| 12 | $C_{20}H_{27}NSCl$ | 62.50 | 7.03 | 3.65 | 18.50 | 62.07 | 7.13 | 3.42 | 18.72 |
| 13 | $C_{22}H_{32}NSCl$ | 69.93 | 8.48 | 3.71 | 9.40 | 69.84 | 8.32 | 3.47 | 9.63 |
| 14 | $C_{22}H_{32}NOCl$ | 73.03 | 8.85 | 3.87 | 9.82 | 72.86 | 8.78 | 3.59 | 10.10 |
| 15 | $C_{22}H_{30}NO_2SCl$ | 64.80 | 7.36 | 3.44 | 8.71 | 64.63 | 7.44 | 3.21 | 9.07 |
| 16 | $C_{21}H_{28}NCl$ | 76.46 | 8.50 | 4.25 | 10.77 | 75.92 | 8.46 | 3.93 | 10.47 |
| 17 | $C_{21}H_{28}NCl$ | 76.46 | 8.50 | 4.25 | 10.77 | 76.23 | 8.51 | 4.10 | 10.63 |
| 18 | $C_{23}H_{33}NS$ | 77.75 | 9.30 | 3.94 | | 77.50 | 9.54 | 3.93 | |
| 19 | $C_{23}H_{33}NS$ | 77.75 | 9.30 | 3.94 | | 77.94 | 9.58 | 3.84 | |
| 20 | $C_{20}H_{28}NSCl$ | 68.67 | 8.01 | 4.00 | 10.16 | 68.78 | 8.26 | 3.87 | 10.17 |
| 21 | $C_{20}H_{28}NSCl$ | 68.67 | 8.01 | 4.00 | 10.16 | 68.92 | 8.00 | 3.77 | 10.39 |
| 22 | $C_{20}H_{28}NSCl$ | 68.67 | 8.01 | 4.00 | 10.16 | 68.55 | 8.01 | 3.94 | 10.20 |
| 23 | $C_{20}H_{28}NSCl$ | 68.67 | 8.01 | 4.00 | 10.16 | 68.29 | 8.20 | 3.93 | 10.06 |
| 24 | $C_{20}H_{28}NSCl$ | 68.67 | 8.01 | 4.00 | 10.16 | 68.27 | 8.01 | 3.94 | 10.21 |
| 25 | $C_{20}H_{28}NSCl$ | 68.67 | 8.01 | 4.00 | 10.16 | 68.20 | 8.18 | 3.77 | 10.02 |

TABLE 3-continued

| n° | crude formula | Percentage Analyses | | | | | | | |
|---|---|---|---|---|---|---|---|---|---|
| | | theoretical | | | | experimental | | | |
| | | C | H | N | Cl | C | H | N | Cl |
| 26 | $C_{19}H_{25}NOS$ | 71.03 | 8.19 | 4.02 | | 71.10 | 8.23 | 3.95 | |

TABLE 4

| COMPOUND | $[^3H]$ BTCP $IC_{50}(nM)$ | $[^3H]$ DA $IC_{50}(nM)$ | $[^3H]$ TCP $IC_{50}(\mu M)$ | Selectivity $IC_{50}[^3H]$ TCP $IC_{50}[^3H]$ BTCP |
|---|---|---|---|---|
| BTCP | 8.4 | 13.9 | 20 | 2380 |
| N° 2 | 13.3 | 9.3 | 52 | 3910 |
| N° 3 | 7.2 | 12.9 | 424 | 58889 |
| N° 4 | 19.1 | 33.8 | 40 | 2094 |
| N° 5 | 35.5 | 65.7 | >>100 | >>2816 |
| N° 6 | 12.7 | 14.9 | >>100 | >>7874 |
| N° 7 | 30.8 | 11.5 | — | — |
| N° 8 | 16.7 | 20.1 | — | — |
| N° 9 | 18.1 | 20.9 | | |
| N° 10 | 34.5 | 57.1 | >>100 | >>2898 |
| N° 11 | 26 | 54.3 | >>100 | >>3846 |
| N° 12 | 102 | 107 | | |
| N° 13 | 635 | 425 | | |
| N° 14 | 2210 | 2740 | | |
| N° 15 | 24.0 | 44.5 | | |
| N° 16 | 14.8 | 36.3 | | |
| N° 17 | 2560 | 3250 | | |
| N° 20 | 20.7 | 21.4 | 112 | 5410 |
| N° 21 | 6.9 | 9.4 | >>100 | >>14493 |
| N° 22 | 369 | 691 | | |
| N° 23 | 590 | 606 | | |
| N° 24 | 14.7 | 30.6 | | |
| N° 25 | 1480 | 1280 | | |
| N° 26 | 15.9 | — | 31.9 | 2006 |
| Nomifensine[1] | 140 | 77 | 95 | 679 |
| Haloperidol[2] | 1670 | — | 520 | 311 |

[1] DA recapture inhibitor
[2] Dopaminergic system inhibitor

TABLE 5

| Compound | EXAMPLE 37 3H-NA capture $IC_{50}$ (nM) | Compound | EXAMPLE 38 Locomotor activity, variation (%) based on controls (100%) for dose 10 mg/kg i.p. |
|---|---|---|---|
| BTCP | 18.3 ± 0.7 | BTCP | +122 ± 12 |
| N° 2 | 40 ± 0.5 | 2 | +160 ± 25 |
| N° 3 | 22.7 ± 1 | 3 | +53 ± 23 |
| N° 4 | 22.2 ± 2.6 | 4 | +169 ± 19 |
| N° 6 | 12.5 ± 1 | 6 | +84 ± 12 |
| N° 10 | 196 ± 31 | 8 | +52 ± 21 |
| N° 20 | 94.3 ± 7.3 | 9 | +416 ± 36 |
| N° 21 | 16.5 ± 1.1 | 10 | +30 ± 19 |
| | | 16 | +269 ± 57 |
| | | 20 | +40 ± 22 |
| | | 21 | +175 ± 27 |
| | | 24 | +101 ± 23 |
| | | 26 | +252 ± 45 |

TABLE 6

| COMPOUND | Toxicity at 100 mg/kg i.p., % mortality at 48 h |
|---|---|
| BTCP | 0 |
| N° 2 | 10 |
| N° 3 | 0 |
| N° 4 | 10 |
| N° 6 | 10 |
| N° 10 | 0 |
| N° 20 | 0 |
| N° 21 | 0 |

TABLE 7

| Compound | $(^3H)$DA Recapture | | $(^3H)$NA Recapture | |
|---|---|---|---|---|
| | IC 50[1] | nH[2] | IC 50[1] | nH[2] |
| n° 2 | 70 nM | 0.95 | — | — |
| n° 3 | — | — | 6.2 μM | 0.85 |
| n° 6 | 1.47 nM | 0.95 | 10.5 nM | 1.2 |
| n° 21 | 8 nM | 1.07 | — | — |
| n° 26 | 17 nM | 1.09 | — | — |

[1] $IC_{50}$ is the concentration of the compound inhibiting 50% of the specific bond of the radioactive ligand.
[2] nH: Hill number.

TABLE 8

Inhibiting the fixing of $(^3H)$BTCP in vivo ($ID_{50}$) in the mouse stratum.

| Compound | $ID_{50}$ (mg/kg) | 95% of limits | Hill number |
|---|---|---|---|
| (BTCP) | 4.98 | (3.41–5.35) | 1.12 |
| n° 4 | 7.78 | (6.34–19.14) | 1.13 |
| n° 16 | 2.66 | (1.61–4.10) | 0.84 |
| n° 26 | 0.56 | (0.4–0.74) | 0.74 |

We claim:

1. Substituted amine in accordance with the formula:

wherein
a) Y represents a nitrogen atom or C—$R_6$, and
  i) when Y represents N,
   $R^1$ and $R^2$, which can be the same or different, represent
    a $C_1$-$C_4$ alkyl radical, or
    a $C_1$-$C_4$ alkyl radical substituted by at least one substituent selected from the group consisting of halogen atoms, the $C_1$-$C_3$ alkoxy radicals and the hydroxyl radical, and
  ii) when Y represents C—$R^6$,
   $R^6$ represents
    a hydrogen atom,
    a $C_1$-$C_4$ alkyl radical,
    a hydroxyl radical or
    a $C_1$-$C_3$ alkoxy radical, and
   $R^1$ and $R^2$ form, with the nitrogen atom to which they are bonded, a piperidine cycle optionally substituted with one to two substituents selected from the group consisting of hydroxyl radical, aralkyl radicals having $C_1$-$C_4$ alkyl portions and phenyl or diphenyl aryl portions, the unsubstituted $C_1$-$C_4$ alkyl radicals, and the $C_1$-$C_4$ alkyl radicals substituted by at least one substituent selected from the group consisting of the halogen atoms, the hydroxy radical, $C_1$-$C_3$ alkoxy radicals, arylalkoxy radicals having $C_1$-$C_3$ alkoxy portions and phenyl or diphenyl aryl portions, and a radical selected from the group consisting of radicals of the formula:

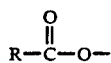

wherein R is $C_1$-$C_4$ alkyl, or optionally having directly attached to the piperidine ring carbon an oxo radical or a spiro radical:

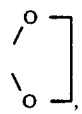

b) $R^3$ is a hydrogen atom or a radical selected from the group consisting of the $C_1$-$C_4$ alkyl, $C_1$-$C_3$ alkoxy and hydroxy radicals, provided that when Y=N, $R^3$ is selected from the group consisting of hydrogen atom or a $C_1$-$C_4$ alkyl radical, c) $R^4$ is selected from the group consisting of a $C_1$-$C_4$ alkyl, hydroxy or $C_1$-$C_3$ alkoxy radical, where n is equal to 0 or is an integer from 1 to 8, whereby the $R^4$ radicals can differ when n is greater than or equal to 2, and d) $R^5$ represents a radical selected from the group consisting of the radicals complying with the formula:

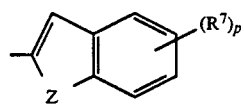

wherein Z is a sulphur or oxygen atom, $R^7$ is a $C_1$-$C_4$ alkyl radical, p is equal to 0, 1 or 2 and the $R^7$ radicals can be different when p=2, provided that $R^3$ does not represent a hydrogen atom when both Y represents —CH and $R^5$ represents

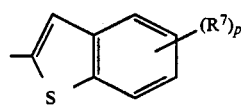

wherein n and p are equal to zero, and $R^1$ and $R^2$ form together with the nitrogen atom to which they are bonded an unsubstituted piperidine cycle.

2. Substituted amine in accordance with the formula:

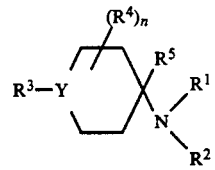

wherein a) Y represents a nitrogen atom or C—$R_6$, and
  i) when Y represents N,
    $R^1$ and $R^2$, which can be the same or different, represent
      a $C_1$-$C_4$ alkyl radical or
      a $C_1$-$C_4$ alkyl radical substituted by at least one substituent selected from the group consisting of halogen atoms, the $C_1$-$C_3$ alkoxy radicals and the hydroxyl radical, or
  ii) when Y represents C—$R^6$,
    $R^6$ represents
      a hydrogen atom,
      a $C_1$-$C_4$ alkyl radical,
      a hydroxyl radical or
      a $C_1$-$C_3$ alkoxy radical, and
    $R^1$ and $R^2$ form, with the nitrogen atom to which they are bonded, a piperidine cycle optionally substituted with one to two substituents selected from the group consisting of hydroxyl radical, aralkyl radicals having $C_1$-$C_4$ alkyl portions and phenyl or diphenyl aryl portions, the $C_1$-$C_4$ alkyl radicals unsubstituted, and the $C_1$-$C_4$ alkyl radicals substituted by at least one substituent selected from the group consisting of the halogen atoms, the hydroxy radical, $C_1$-$C_3$ alkoxy radicals, arylalkoxy radicals having $C_1$-$C_3$ alkoxy portions and phenyl or diphenyl aryl portions, and, a radical selected from the group consisting of radicals of the formula:

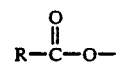

wherein R is $C_1$-$C_4$ alkyl, or optionally having directly attached to the piperidine ring carbon an oxo radical or a spiro radical:

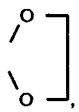

b) $R^3$ is a hydrogen atom or a radical selected from the group consisting of the $C_1$-$C_4$ alkyl, $C_1$-$C_3$ alkoxy and hydroxy radicals, provided that when Y=N, $R^3$ is selected from the group consisting of a hydrogen atom or a $C_1$-$C_4$ alkyl radical, c) R$^4$ is selected from the group consisting of a C$_1$–C$_4$ alkyl, hydroxy or C$_1$–C$_3$ alkoxy radical, n is equal to 0 or is an integer from 1 to 8, whereby the R$^4$ radicals can differ when n is greater than or equal to 2, and d) R$^5$ represents a radical selected from the group consisting of the radicals complying with the formula:

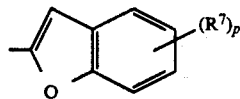

in which R$^7$ is a C$_1$–C$_4$ alkyl radical, p is equal to 0, 1 or 2 and the R$^7$ radicals can be different when p=2.

3. Substituted amine according to claim 1, wherein R$^5$ represents the radical of formula:

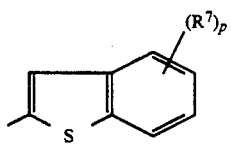

(V)

in which R$^7$ and p have the meanings given in claim 1.

4. Substituted amine according to claim 3, wherein p=0.

5. Substituted amine according to claim 3, wherein Y represents CH.

6. Substituted amine according to claim 4, wherein R$^3$ is a hydrogen atom, a methyl radical or an ethyl radical.

7. Substituted amine according to claim 3, wherein R$^1$ and R$^2$ form, together with the nitrogen atom to which they are bonded, a piperidine cycle, which is either unsubstituted or substituted by at least one alkyl radical.

8. Substituted amine according to claim 3, wherein R$^1$ and R$^2$ are alkyl radicals.

9. Substituted amine according to claim 7, wherein it is 1-(2-benzo(b)thiophenyl)-c-methyl-4-r-(1-piperidino)-1-cyclohexane.

10. Substituted amine according to claim 7, wherein it is 1-(2-benzo(b)thiophenyl)-1-(3-methyl-1-piperidino)-cyclohexane.

11. Substituted amine according to claim 7, wherein it is 1-(benzo(b)thiophenyl)-1-(3,5-dimethyl-1-piperidino)-cyclohexane.

12. Substituted amine according to claim 2, wherein it is 1-(2-benzo(b)furanyl)-1-(1-piperidino)-cyclohexane.

13. Pharmaceutical composition comprising as an active ingredient at least one substituted amine according to claim 1 or an addition salt to an acid of said amine, and a pharmacologically suitable carrier, said active ingredient being present in an effective amount for treatment of dopaminergic-dependent conditions.

* * * * *